United States Patent
Duan

(10) Patent No.: US 11,129,518 B2
(45) Date of Patent: Sep. 28, 2021

(54) PORTABLE SYSTEM AND METHOD FOR POSITION AND ORIENTATION OF REMOTE OBJECTS

(71) Applicant: Xiaodong Duan, Pleasanton, CA (US)

(72) Inventor: Xiaodong Duan, Pleasanton, CA (US)

(73) Assignee: Ankon Medical Technologies (Shanghai) Co., LTD., Shanghai (CN)

( * ) Notice: Subject to any disclaimer, the term of this patent is extended or adjusted under 35 U.S.C. 154(b) by 535 days.

(21) Appl. No.: 15/972,111

(22) Filed: May 5, 2018

(65) Prior Publication Data

US 2019/0335983 A1 Nov. 7, 2019

(51) Int. Cl.
  *A61B 1/00* (2006.01)
  *A61B 1/04* (2006.01)
  *G01R 33/09* (2006.01)
  *G01R 33/07* (2006.01)
  *G01R 33/02* (2006.01)

(52) U.S. Cl.
  CPC .......... *A61B 1/00158* (2013.01); *A61B 1/041* (2013.01); *G01R 33/0206* (2013.01); *G01R 33/072* (2013.01); *G01R 33/091* (2013.01)

(58) Field of Classification Search
  CPC .. A61B 1/00158; A61B 1/041; G01R 33/091; G01R 33/072; G01R 33/0206; G01R 33/025; G01R 33/0017
  See application file for complete search history.

(56) References Cited

U.S. PATENT DOCUMENTS

| | | | |
|---|---|---|---|
| 2005/0216231 A1* | 9/2005 | Aoki | A61B 1/00158 702/183 |
| 2006/0152309 A1* | 7/2006 | Mintchev | A61B 5/073 335/58 |
| 2008/0139883 A1* | 6/2008 | Uchiyama | A61B 1/041 600/117 |

(Continued)

OTHER PUBLICATIONS

Pham et al. "A Real-Time Localization System for an Endoscopic Capsule Using Magnetic Sensors", Nov. 5, 2014, pp. 20911-20927 (Year: 2014).*

(Continued)

*Primary Examiner* — John E Breene
*Assistant Examiner* — Eyob Hagos
(74) *Attorney, Agent, or Firm* — Treasure IP Group, LLC

(57) ABSTRACT

The present invention describes an electromagnetically positioning system, which can measure a position and orientation of a remote object in an isolated targeted examination area with time. Specifically, the remote object is a remote miniaturized examination device. During the location process, both the electromagnetically positioning system and the remote miniaturized examination device can have expected or unexpected, controlled and can-not-be-controlled movement. By implementing the electromagnetically positioning system, disclosed herein, position and orientation information of the remote miniaturized examination device can be linked with time, any information collected by the remote miniaturized examination device, for example, the photo images collected, can be associated kinetically with time and positioning information of the examination device, when the remote miniaturized examination device travels inside an isolated target examination area.

7 Claims, 13 Drawing Sheets

(56) References Cited

U.S. PATENT DOCUMENTS

| | | | | |
|---|---|---|---|---|
| 2009/0318762 A1* | 12/2009 | Segawa | A61B 1/041 | 600/118 |
| 2010/0204566 A1* | 8/2010 | Uchiyama | A61B 5/06 | 600/424 |
| 2012/0095290 A1* | 4/2012 | Kawano | A61B 1/041 | 600/117 |
| 2012/0277529 A1* | 11/2012 | Popescu | A61B 1/00158 | 600/109 |
| 2013/0267788 A1* | 10/2013 | Duan | G01B 7/003 | 600/300 |
| 2013/0303847 A1* | 11/2013 | Sitti | A61B 1/00158 | 600/104 |
| 2014/0187907 A1* | 7/2014 | Duan | G01B 7/14 | 600/409 |
| 2015/0138329 A1* | 5/2015 | Braun | A61B 5/073 | 348/71 |
| 2015/0380140 A1* | 12/2015 | Duan | A61B 1/041 | 600/109 |
| 2016/0135668 A1* | 5/2016 | Gat | A61B 5/062 | 600/118 |
| 2016/0143514 A1* | 5/2016 | Mahoney | A61B 5/062 | 600/409 |
| 2017/0202479 A1* | 7/2017 | Khait | A61B 5/062 | |
| 2018/0042519 A1* | 2/2018 | Chiba | A61B 1/041 | |
| 2018/0084975 A1* | 3/2018 | Duan | A61B 1/041 | |

OTHER PUBLICATIONS

Zhang et al. "Study on the system of a capsule endoscope driven by an outer rotational magnetic field", IEEE 2006, pp. 1-5 (Year: 2006).*

Popek et al. "Localization Method fora Magnetic Capsule Endoscope Propelled by a Rotating Magnetic Dipole Field", May 2013, IEEE, pp. 5348-5353 (Year: 2013).*

Song et al. "6-D Magnetic Localization and Orientation Method for an Annular Magnet Based on a Closed-Form Analytical Model", Sep. 2014, IEEE, pp. 1-12 (Year: 2014).*

* cited by examiner

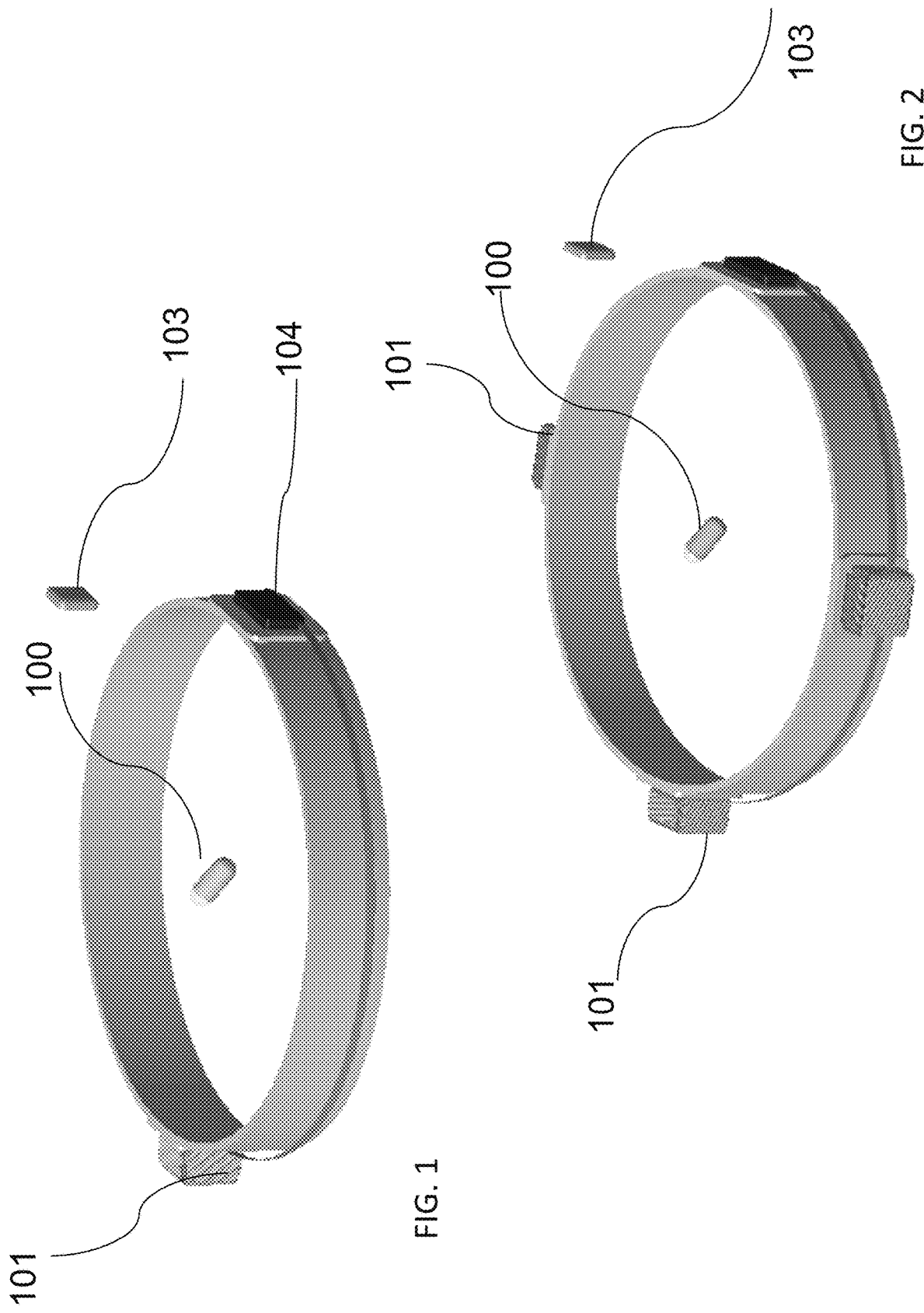

CAPSULE

REFERENCE

α is the rotation around X axis, called pitch
β is the rotation around Y axis, called yaw
γ is the rotation around Z axis, called roll

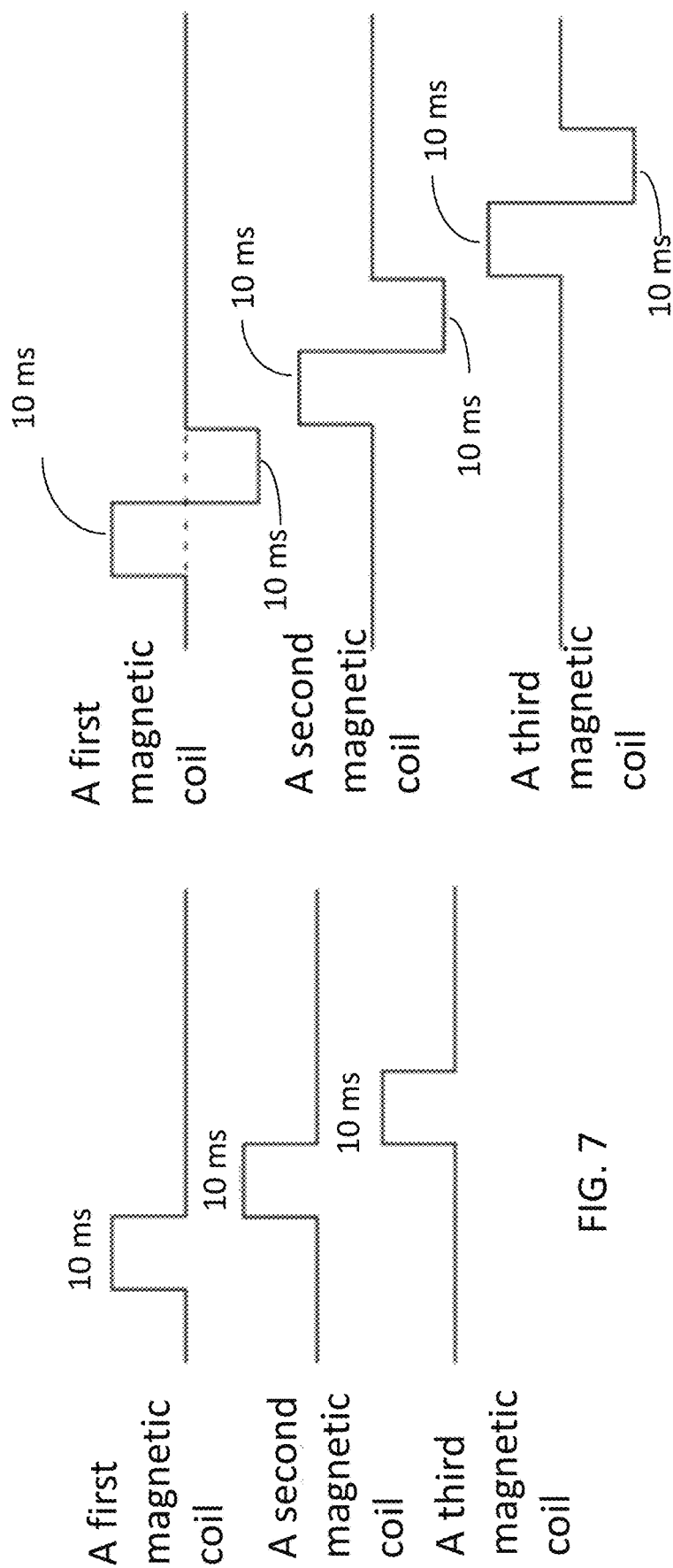

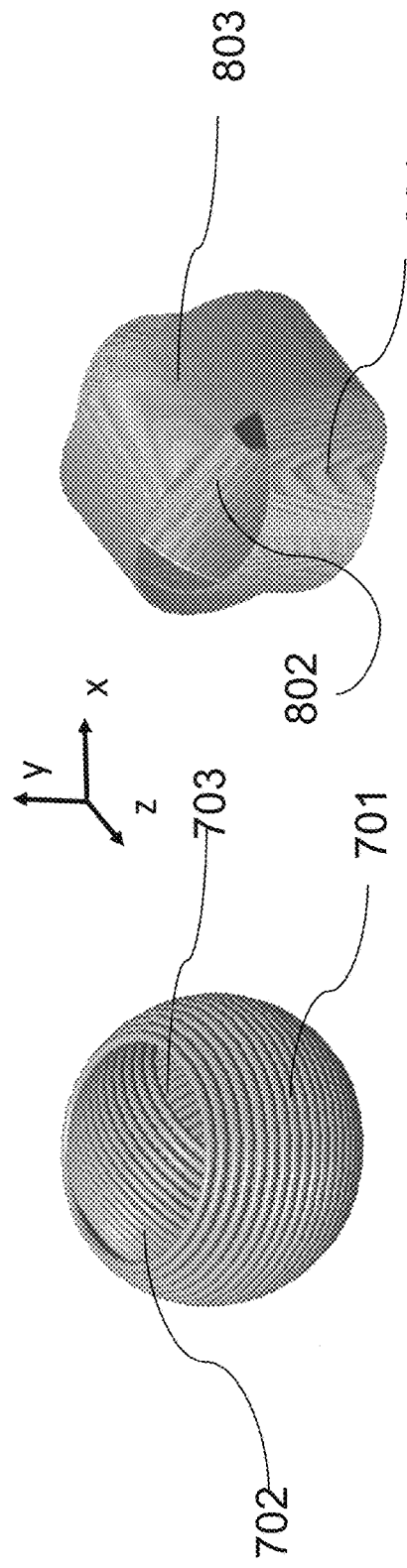
Figure 9
Figure 10
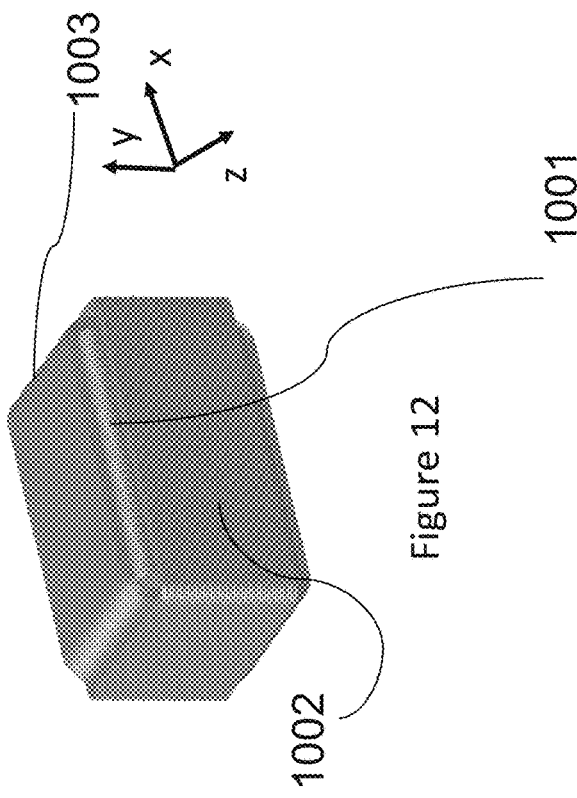
Figure 11
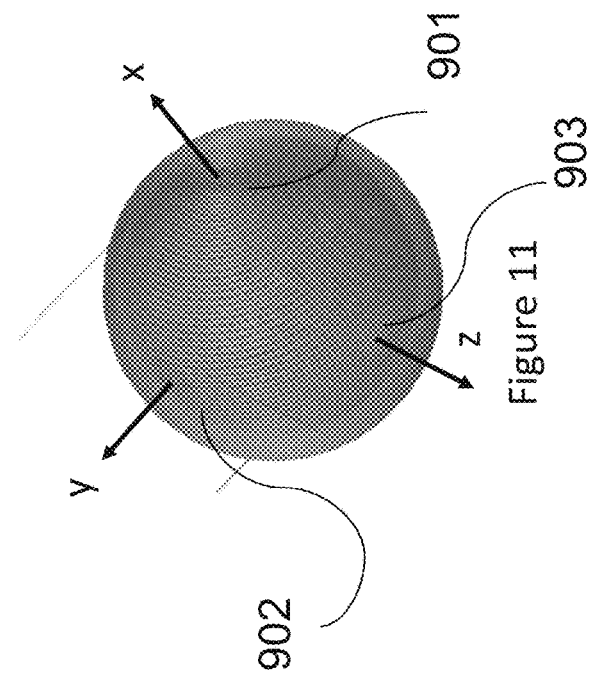
Figure 12

Rotation about Left(X) Axis (Pitch)

Rotation about Up(Y) Axis (Yaw, Heading)

Rotation about Forward(Z) Axis (Roll)

PORTABLE SYSTEM AND METHOD FOR POSITION AND ORIENTATION OF REMOTE OBJECTS

CROSS REFERENCE

None.

TECHNICAL FIELD

The invention relates to use of magnetic fields for orientation and movement of remote objects. More particularly, the invention relates to systems and methods for determining a position of a remote miniaturized examination device using a portable magnetic generation system.

BACKGROUND OF THE INVENTION

The deployment of relatively small probes or sensors for performing tasks in confined, inaccessible, or remote spaces is useful in several contexts. For example, it is known in the arts to use wireless remote miniaturized examination devices for collecting images by equipping them with cameras, or for delivering doses of medication to general areas of the digestive system by equipping them with drug reservoirs. The currently available wireless remote miniaturized examination devices used in the medical field are carried by peristalsis through the digestive tract. In non-medical applications, a probe remote miniaturized examination device may be carried by fluid flow and/or gravity through a system of piping or tubing. Such approaches utilize movement inherent in the environment being investigated, and the movement and orientation of the probes is left to chance to some extent. The challenges of providing controllable location and orientation for remote probe technology are significant. Attempts to provide movement capabilities to remote probes have been made using mechanical drive systems. However, such systems require a significant amount of power, which is difficult to provide within the space available. In recent years, magnetic control system through interaction between a permanent magnetic dipole placed in situ in the remote miniaturized examination device and an external magnetic control system have been developed. However, the use of permanent magnetic dipole adds dimension and weight to the remote miniaturized examination device, and the external magnetic control systems are expensive, it is important to have alternative methods to detect position of a remote miniaturized examination device endoscope.

It is known that an electromagnetically positioning system can be used to measure a remote miniaturized examination device location remotely in a digestive tract. The electromagnetically positioning system, disclosed therein, includes a sealed remote miniaturized examination device having a three-dimensional magnetic field sensor, signal processing module and radio communication module, and three external magnetic field exciting coils, and external data recording device. During the electromagnetically positioning system operation, the three coils are fixed onto the surface of a patient's body, and the three coils will generate magnetic field successively under the excitation of the current, the remote miniaturized examination device in the digestive tract detects the external magnetic fields and produces and emits the data to the recording device. By doing so, the recorder receives both information relating to both the external exciting coil and remote miniaturized examination device at a time, therefore the journey of the remote miniaturized examination device in the digestive tract can be traced.

Due to the foregoing and possibly additional problems, improved apparatus, systems and methods for orientation and movement of remote objects would be useful contributions to the arts. Further, in view of the foregoing, a system and method that can accurate detect a position and orientation of a remote object during a process either the system or the remote project can move predictably or unpredictably is needed.

SUMMARY OF THE INVENTION

The present invention discloses an electromagnetically positioning system, which can measure a position and orientation of a remote object in an isolated targeted examination area with time. Specifically, the remote object is a remote miniaturized examination device. During the location process, both the electromagnetically positioning system and the remote miniaturized examination device can have expected or unexpected, controlled and can-not-be-controlled movement. By implementing the electromagnetically positioning system, disclosed herein, position and orientation information of the remote miniaturized examination device can be linked with time, any information collected by the remote miniaturized examination device, for example, the photo images collected, can be associated kinetically with time and positioning information of the examination device, when the remote miniaturized examination device travels inside an isolated target examination area.

It is one object of the present invention, to provide a system for determining the position of a remote object electromagnetically, which can trace the remote object and its movement data in a target isolate area.

It is another object of the present invention, to provide a system for determining the position of a remote object electromagnetically, which can take high quality photographical images to be labelled with time or geographical information kinetically as the remote miniaturized examination device travels through the isolated targeted examination area. By doing so, a remote object having an imaging means can be programmed to take pictures with a predetermined location interval or to be programmed in real time, so that a total number of the photographical images of the isolated targeted examination area that needs to be taken and processed are significantly reduced.

It is still another object of the present invention, to provide a portable system for determining the position of a remote object electromagnetically that offers low energy consumption rate in the remote object, so that the remote object can work unanimously and efficiently throughout its journey in the remote area. The low energy consumption rate is achieved by intelligently turning on the remote object to work state or reducing the total number of high energy consumption work functions, for example, taking pictures selectively to reduce the total number of pictures that need to be taken, without sacrificing the quantity and quality of the information received.

It is yet another object of the present invention, to provide a portable system for determining the position of a remote object electromagnetically that the portable external magnetic field generation assembly can be easily brought near to the remote area or disposed to cover the remote area, when it is in use, without additional physical mechanical fixtures.

The portable system can work accurately indoors or in the open field, with little sensitive to environment.

It is still another object of the present invention, to provide a portable system for determining the position of a remote object electromagnetically that the portable external magnetic field generation assembly can accurately detect the position of the remote object regardless if the portable system is in a stationary status or movement status. Further, regardless if the movement of the remote object is synchronized with the movement of the portable system, the location information obtained from the measurement system and calculation method disclosed herein can be trustworthy.

According to a first aspect of the present invention, a portable electromagnetically positioning system is disclosed. The portable electromagnetically positioning system comprises a remote miniaturized examination device, configured to be placed in situ, in an isolated target examination area, having a first 3-dimensional magnetic field sensor, a signal processing module and wireless communication module. The portable electromagnetically positioning system further comprises a portable external magnetic field generation assembly, which can generate pulsed magnetic fields respectively in three dimensions, and the pulsed magnetic fields generated externally can be sensed by the first 3-dimensional magnetic field sensor. Optionally, the electromagnetically positioning system comprises a reference position unit including at least a second 3-dimensional magnetic field sensor, configured to be placed on a support surface external to the isolated target remote area. The second 3-dimensional magnetic field sensor, is placed at the external support surface at a predetermined location and fixed direction when the remote object travels inside the remote isolated target area. Additionally, the electromagnetically positioning system comprises a mobile recorder. Said mobile recorder sends instruction to the three-dimensional coil assembly and receives information from the remote object.

In one embodiment, according to the first aspect of the present invention, the remote object is a remote miniaturized examination device.

In another embodiment, according to the first aspect of the present invention, the portable external magnetic field generation assembly is a three-dimensional excitation coil assembly, which generates pulsed magnetic fields three dimensionally. The three-dimensional excitation coil assembly can generate a magnetic field in the range of 0.02-12 Gauss. In the embodiment disclosed herein, the three-dimensional excitation coil assembly is configured to be placed 3-20 cm apart from the remote object or remote miniaturized examination device.

In one example, the three-dimensional excitation coil assembly have three sets of coils, each winding around an axis and each axis being perpendicular to two other axes, and three axes intersecting at a center of the three-dimensional excitation coil assembly, wherein the three-dimensional excitation coil assembly is in a shape of a globe, or cubic. Preferably, the distance from the center of a three-dimensional excitation coil to the center of the remote object about 10 cm.

In a preferred embodiment, according to the first aspect of the present invention, the external magnetic field generation assembly is can be easily brought near to the remote area or disposed to cover the remote area without additional physical mechanical fixtures.

In still another embodiment, according to the first aspect of the present invention, the portable external magnetic field generation assembly comprises three three-dimensional excitation coil assemblies, each is made of an excitation coil wounded in x, y and z directions.

According to a second aspect of the present invention, a method of using the electromagnetically positioning system to accurately detect and calculate the position of the remote object is disclosed. The method includes a first step of determining three "pure" magnetic fields generated by three-dimensional magnetic excitation assembly, a second step of calculating the position of the remote object and a third step of determining orientation of the remote object.

Three alternative methods to determine three "pure" magnetic fields generated by three-dimensional magnetic excitation assembly are disclosed. A first method involves measuring the environmental magnetic field data and removing the environmental magnetic field data from the measured total magnetic field data of the three-dimensional magnetic assembly.

A second method involves measuring total magnetic field data using a bipolar pulsed sequencing method, wherein the environmental magnetic field data is measure in a positive and negative direction, and the addition results of the two total magnetic field data lead to cancellation of the environmental magnetic field.

A third method involves using a combinatorial sequencing method to measure the total magnetic fields three times, and among which at least one electrical current direction for one of the coil is different from the previous sequence.

Further, in the embodiment of obtaining an environmental magnetic field by subtracting environmental magnetic field from the total magnetic field, including, in one embodiment, measuring a first environmental magnetic field before measuring a total magnetic field. In another embodiment, determining an environmental magnetic field including measuring a second environmental magnetic field after the step of generating pulsed magnetic field. In a preferred embodiment, determining an environmental magnetic field including measuring a first environmental magnetic field before the step of generating pulsed magnetic field; measuring a second environmental magnetic field after the step of generating pulsed magnetic field; taking an average the first and second environmental magnetic field data as the environmental magnetic field.

In carrying out the principles of the present invention, in accordance with preferred embodiments, the invention provides a portable system and easy to use methods to allow the information generated or collected by the remote object to be labeled with geographical or condition information in real time. The portable system and easy to use methods disclosed herein can trace the movement of the remote object in the isolated area in real time or predetermined time intervals. With the detectable and reliable geographical information, like position and/or orientation, of the remote object, and effective wireless communication module, an operator or artificial intelligence interface can interact with the remote object make the remote object work more intelligently and efficiently to collect more relevant information fits to the designed purpose.

The invention has advantages including but not limited to providing one or more of the following features, orientation control for remote objects, controlled movement for remote objects, low power consumption requirements for probe motion systems, and robustness of motion control and data collection elements. These and other advantages, features, and benefits of the invention can be understood by one of ordinary skill in the arts upon careful consideration of the detailed description of representative embodiments of the invention in connection with the accompanying drawings.

BRIEF DESCRIPTION OF THE DRAWINGS

The present invention will be more clearly understood from consideration of the description and drawings in which:

FIG. 1 is a schematic illustration of a first exemplar embodiment of the electromagnetically positioning system, in accordance with the aspects of the present invention;

FIG. 2 is a schematic illustration of a second exemplar embodiment of the electromagnetically positioning system, in accordance with the aspects of the present invention;

FIG. 7 is one embodiment of the pulsed sequence to turn on and off the three-dimensional excitation coil assembly;

FIG. 8 is another embodiment of the pulsed sequence to turn on and off the three-dimensional excitation coil assembly;

FIGS. 9-12 are examples of three-dimensional excitation coil assemblies, in accordance with the aspects of the present invention;

Figure 3:
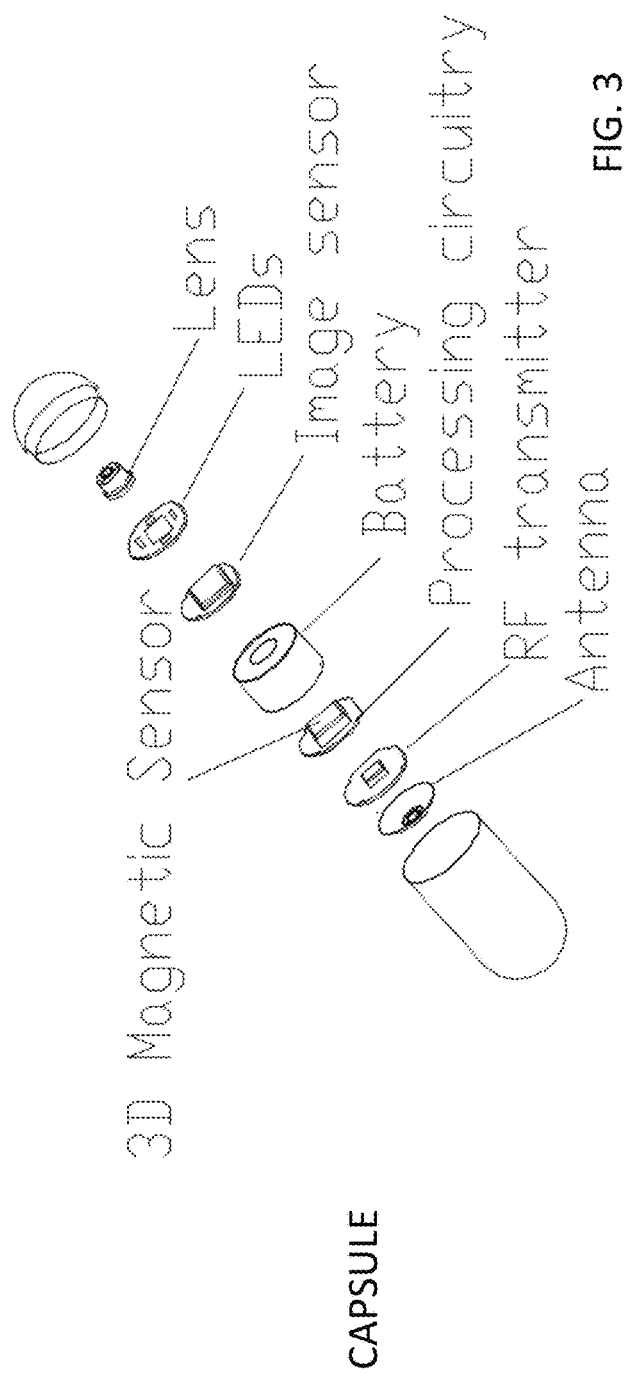
FIG. 3 is a schematic illustration of an exemplar embodiment of the remote object, in exploded view, in accordance with the aspects of the present invention.

References in the detailed description correspond to like references in the various drawings unless otherwise noted. Descriptive and directional terms used in the written description such as up, down, horizontal, vertical, upper, side, et cetera; refer to the drawings themselves as laid out on the paper and not to physical limitations of the invention unless specifically noted. The drawings are not to scale, and some features of embodiments shown and discussed are simplified or amplified for illustrating principles and features as well as advantages of the invention.

DESCRIPTION OF PREFERRED EMBODIMENTS

While the making and using of various exemplary embodiments of the invention are discussed herein, it should be appreciated that the apparatus and techniques for its use exemplify inventive concepts which can be embodied in a wide variety of specific contexts. It should be understood that the invention may be practiced in various applications and embodiments without altering the principles of the invention. For purposes of clarity, detailed descriptions of functions, components, and systems familiar to those skilled in the applicable arts are not included. In general, the invention provides apparatus, systems, and methods for moving and orienting remote objects. The invention is described in the context of representative example embodiments. Although variations and alternatives for the details of the embodiments are possible, each has one or more advantages over the prior art.

For simplicity purpose, the miniaturized examination device disclosed herein is designed to be placed in vivo. The target area is a digestive track. One of the non-invasive methods of delivery is by swallow into a digestive tract. However miniaturized examination device disclose herein should not be construed as a limitation for its shape, dimension or size. The miniaturized examination device and three dimensional excitation coil disclosed herein and methods of using the same can be implemented for many other applications as long as the movement of the miniaturized examination device and excitation coil meet the aspects of the present invention.

For simplicity purposes, solenoid is used in some examples of three-dimensional excitation coil assemblies. In most of the descriptions, solenoid is referred as coils winded around a cylindrical shape body. But within the scope of the present invention, the examples and calculation with reference to a solenoid is for illustration purpose only and should be construed as a limitation.

The 3D solenoids assembly which includes three coils in perpendicular to each other. Three coils have the common geometry center. The shape of the cross section of each coil can be a disc or a square, rectangular, or ellipse or alike. The cross-section area can be the same or slightly different. An example of the variable cross section is a spherical coil or a rectangular shaped three-dimensional coil assembly.

The present invention involves calculation to determine the position of the remote object. In the calculation, all the 3D solenoids assembly are modeled as 3 perpendicular magnetic dipoles. This assumption is typically a good approximation when the distance from a remote object to the center of the coil is 2 times longer than its geometry length. But for the uniform spherical coil, the dipole model is accurate when the distance from the remote object to the center of the spherical coil is longer than its radius. It is an approximation when the measuring points are very close to the solenoid. Our dipole model is good when the distance to the coil is about 2-3 times away from its longest dimension.

In accordance with the aspects of the present application, "portable," in some embodiments, means capable of being borne or carried and easily transported. In some embodiments, "portable," means wearable, suitable for wear or able to be worn. In addition, in some embodiment, "portable" means the electromagnetic system is constantly moved, predictably or in a can-not-be-controlled fashion.

In accordance with the aspects of the present invention, the distance between the magnetic excitation assembly and remote object is defined as the distance from a center of the magnetic excitation assembly to the instant position of the 3-D magnetic sensor in the remote object. The center of the magnetic excitation assembly is defined as a meeting point of the individual magnetic axis of the magnetic excitation assembly. In one example, the center of the magnetic excitation assembly is a geometric center of the magnetic excitation assembly. In another example, the center of the magnetic excitation assembly is not the geometric center of the magnetic excitation assembly.

In accordance with the aspects of the present invention, a 3D magnetic sensor fixed to a remote moving object. The remote moving object comprises a power supply to provide power for the 3D magnetic sensor and a Microprocessor Control Unit which can digitalize the magnetic field sensed by the 3D magnetic sensor, and an optional wireless communication hardware.

In accordance with the aspects of the present invention, in the mathematical calculations to determine the distance and position of the remote object, and other calculations within the scope of the present invention, B is the strength of the magnetic field, in Bx, the first denote, a regular font letter next to B, is the source or owner of the magnetic strength, for example, Bx means the magnetic field strength belongs to the X coil. In $Bx_x$, the second denote, a subscript, is a directional or component magnetic field strength measured by the magnetic sensor. For example, $Bx_x$, means the x component magnetic field strength, of the X coil, measured by the magnetic sensor in the remote object. Further, B having no other superscript, means it is referenced in the coil coordinate. B', with a ' superscript means it is referenced in the 3D magnetic sensor coordinate.

The principles of the invention shown and described may also be applied to additional uses in vivo or to probes used in other contexts such as mechanical or fluid or medical handling or delivery systems. The term "remote miniaturized examination device" is used interchangeably with the term "probe" herein to refer to probe apparatus and similar remote objects in general, regardless of shape. It should be understood that a remote miniaturized examination device may be spherical, cylindrical, substantially cylindrical with hemi-spherical ends, or other suitable shapes or combinations of shapes. The remote miniaturized examination device 100.

According to a first aspect of the present invention, in a first embodiment, a portable electromagnetically positioning system is disclosed. The portable electromagnetically positioning system comprises a remote miniaturized examination device, configured to be placed in situ, in an isolated target examination area, having a first 3-dimensional magnetic field sensor, a signal processing module and wireless communication module. The signal processing module and a wireless communication module can be a RF transmitter and antenna. The remote miniaturized examination device further comprises image sensor, lens and one or more LEDs.

In one example of the first embodiment, there is no permanent magnetic dipole placed inside the remote object. In another example of the first embodiment, a permanent magnetic dipole is placed inside the remote object.

Referring to FIG. 1, the portable electromagnetically positioning system consists essentially a remote miniaturized examination device 100, configured to be placed in an isolated target examination area, having a first 3-dimensional magnetic field sensor, a portable external magnetic field generation assembly 101, capable of generating pulsed magnetic fields respectively in three dimensions, and the pulsed magnetic fields generated externally can be sensed by the first 3-dimensional magnetic field sensor, and a second 3-dimensional magnetic field sensor 103, and a mobile recorder 104, which sends instructions to the portable external magnetic field generation assembly through a coil driving module to operate each coil independently and receives data from the first 3-dimensional magnetic field sensor in the remote miniaturized device. Z axis of the first magnetic sensor in the remote miniaturized examination device coincides with the length direction of the miniaturized examination device.

Referring to FIG. 2, in a similar fashion, the portable electromagnetically positioning system consists essentially a remote miniaturized examination device 100 having a first 3-dimensional magnetic field sensor, three portable external magnetic field generation assemblies 101, a second 3-dimensional magnetic field sensor 103, and a mobile recorder 104.

In both FIGS. 1 and 2, the portable external magnetic field generation assemblies 101 and a mobile recorder 104 are configured to be placed on a support surface external to the isolated target remote area, as a reference magnetic field sensor and the second 3-dimensional magnetic field sensor, is placed at the external support surface with a predetermined location and fixed direction when the remote examination device travels inside the remote isolated target area.

The system described in FIG. 1 and FIG. 2 differs mostly on the number of solenoids which are employed. The system shown in FIG. 2 has three solenoids. Theoretically speaking, a system having one solenoid can pretty much perform the same position measurement as a system having three solenoids. Except that the system having three solenoids offers better precision in location determination and allow a much longer detection range. Because the range of detection depends on the signal noise ratio of the magnetic sensor measurement. To improve the signal to noise ratio, the magnetic moment of the solenoid shall be increased. One way to increase the magnetic moment of the solenoids is to increase the exciting current. Since the magnetic field generated is proportional to the invert of cubic power of the distance from the center of the solenoid to the remote object, in order to double the detection range, the exciting current shall be increased by 8 times. However, for a defined coil setup, a maximum allowed current is limited by the diameter of the wire and the pulse width and the maximum output current of the power supply. The larger of the wire diameter, the larger of current allowed. The shorter of the pulse width, the larger of current allowed. Then the maximum output current of the power supply is the limitation of the current. In other words, once a solenoid is made, the maximum allowed current is clearly defined. Under such a situation, without making a new solenoid, but also extend the detection range, one can accommodate more pulse current by using three solenoids at the same time, instead of just one.

Figure 5:
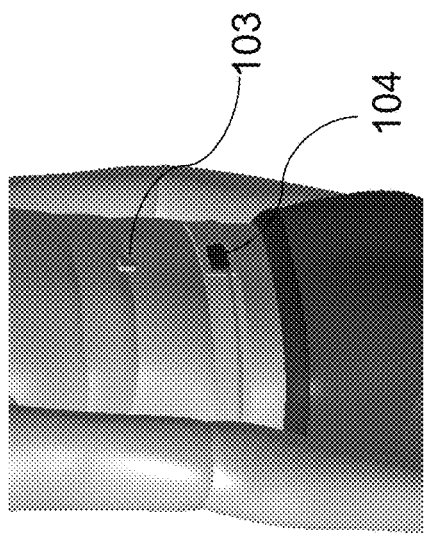
FIG. 5 is a schematic illustration of an exemplar in use situation, the human figure is for illustration purpose and is not part of the invention.

Referring to FIG. 5, external magnetic field generation assemblies 101 and a mobile recorder 104 are secured outside of the target area containing the remote object 100, and surrounding the target area, like on a belt surrounding a patient's waist.

Figure 18:
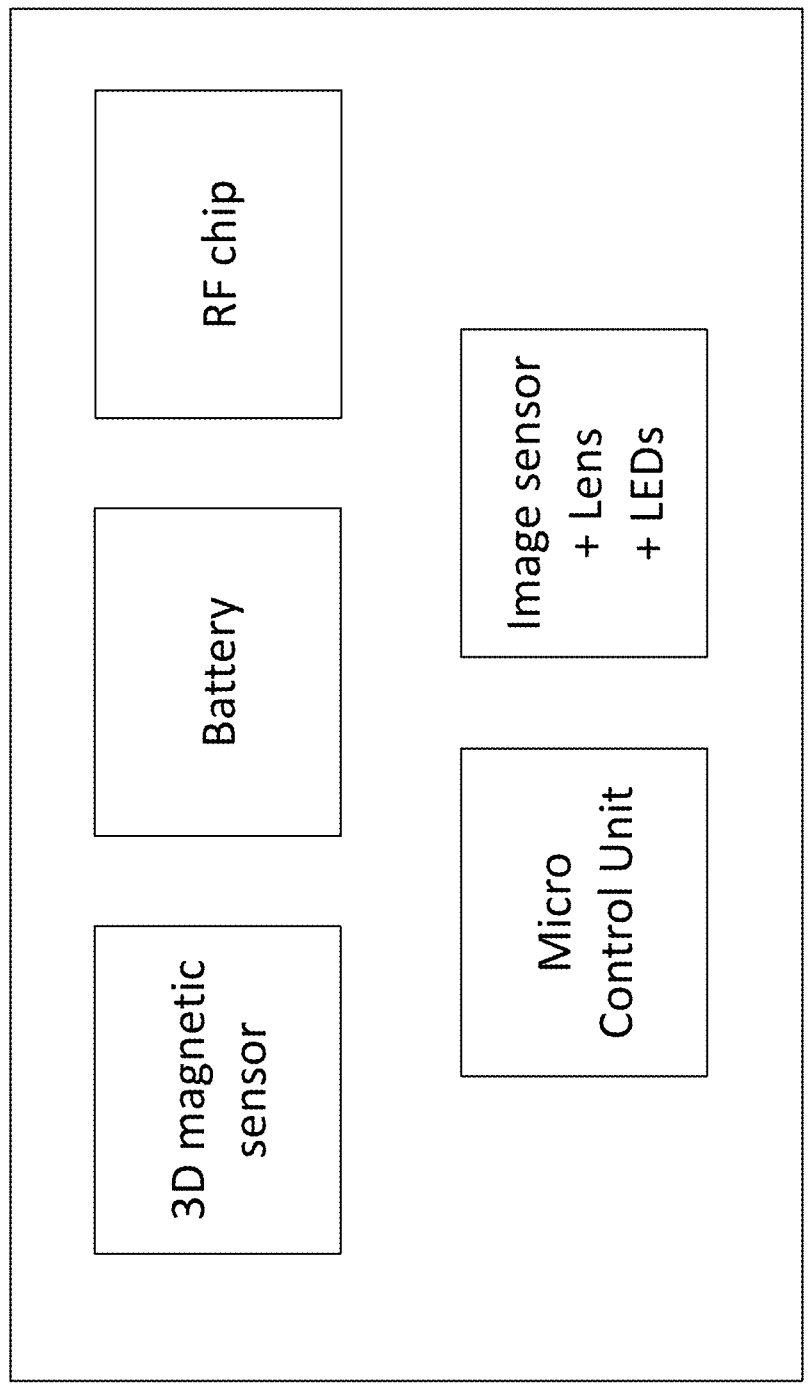
FIG. 18 is a schematic diagram of an exemplar miniaturized medical device, in accordance with the aspects of the present invention.
Figure 19:
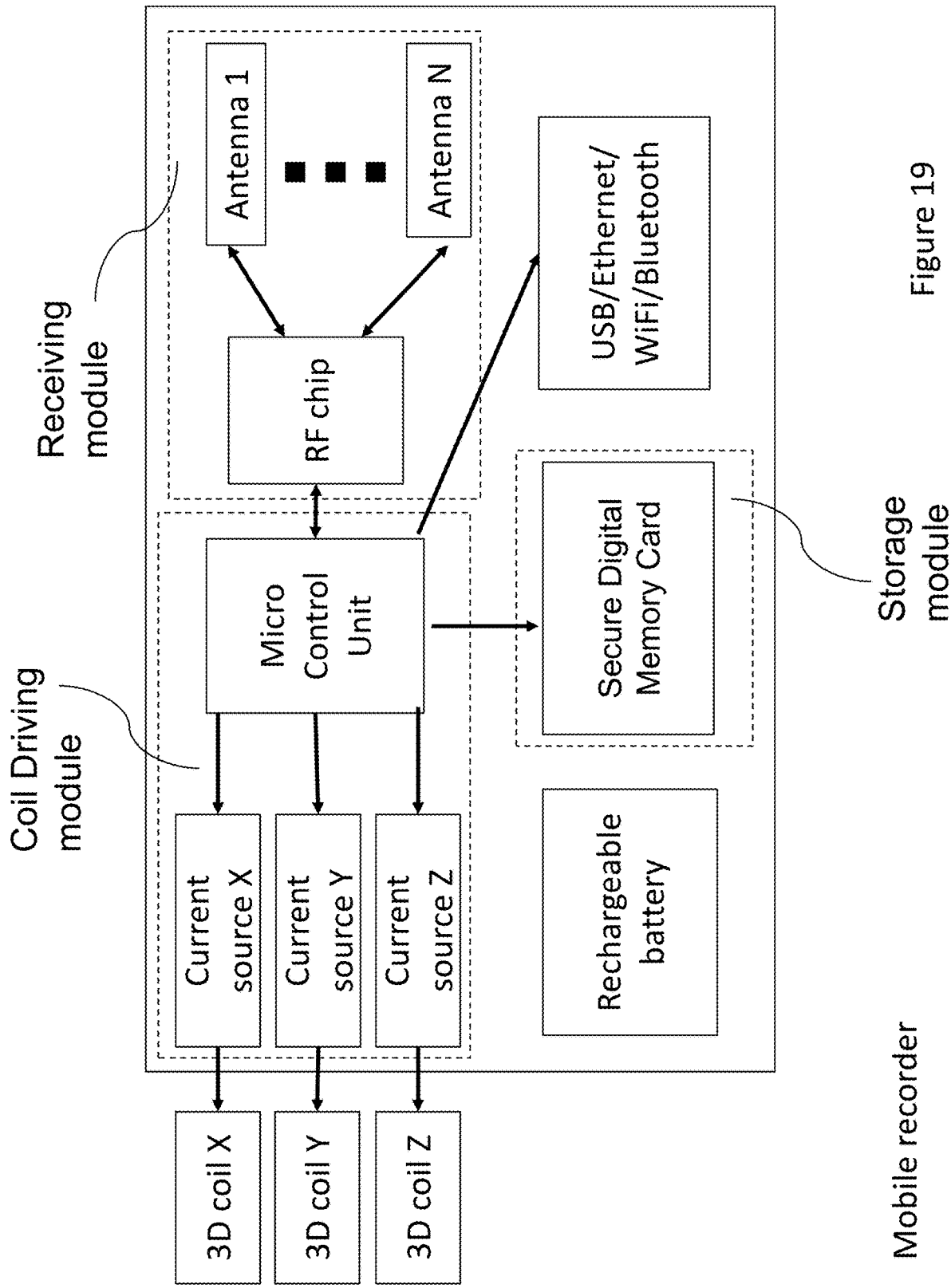
FIG. 19 is a schematic diagram of an exemplar mobile recorder and its interaction with the external coil assembly.

In one example, the miniaturized examination device is a capsule or capsule endoscope. The exemplar structural details of the capsule is schematically illustrated in FIG. 3 and FIG. 18.

Figure 4:
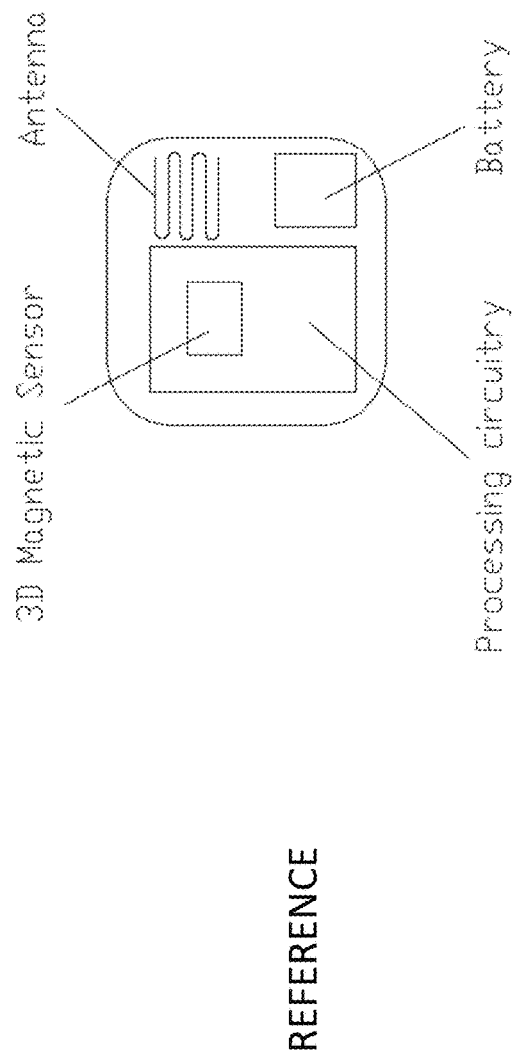
FIG. 4 is a schematic illustration of an exemplar embodiment of the reference position assembly, in accordance with the aspects of the present invention.

Reference sensor disclosed herein is enclosed in a reference sensor assembly, which further includes a processing circuitry, battery and antenna, as shown in FIG. 4.

Three-Dimensional Magnetic Field Sensor

The system and method disclosed herein is for a potable application. In the first embodiment of the first aspect of the invention, a reliable, robust yet highly sensitive three-dimensional magnetic field sensor should be used. The three-dimensional magnetic field sensor has detection limits within several Gaussians and have low operation noise. In absent of a permanent magnetic dipole inside the remote object, the 3D magnetic field sensor should be calibrated to remove the influence of geomagnetic field prior to each measurement.

In accordance with the aspect of the present invention, any three-dimensional magnetic field sensor can be used to accomplish the purpose of the present invention. The three-dimensional magnetic field sensor can be selected from a group of sensors including a 3D magneto-resistive AMR sensor and 6-axis sensors. The appropriate sensor is chosen by considering detection range, sensitivity, noise, power consumption and sampling speed.

One exemplar 3D magneto-resistive AMR sensor is 3D magneto-resistive AMR sensor MMC314xMS, which has a detection range+/−4 Gauss, sensitivity of 2 mGauss, noise less than 0.6 m Gauss, power consumption at 0.55 mA@3V, and read time at 7-10 ms.

One exemplar 6-axis sensor is 6-axis sensor LMS303D, which has a detection range: +/−12Gauss, sensitivity of 0.08 m Gauss, noise less than 5 mGauss, power consumption at 0.3 mA@1.8V, and sampling speed up to 100 Hz.

Another exemplar 6-axis sensor is 6-axis sensor FXOS8700CQ, which has a detection range of +/−12Gauss, sensitivity of 0.18 m Gauss, noise less than 10 m Gauss, power consumption at 0.24 mA@1.8V, and sampling speed up to 800 Hz.

The first 3D-magnetic field sensor(s) 104 is aligned with the external excitation coil assembly in order to sense the x-, y-, and z-axis magnetic field. In this example, the z direction is along the remote miniaturized examination device axis. The magnetic field values sensed with the magnetic field sensor are preferably sent out from the remote miniaturized examination device 100 using an included RF transmitter 106 and antenna 108. Optionally, an image sensor 110, lens 112, and one or more LEDs 114 may be included in the remote miniaturized examination device 100 for medical imaging purposes, along with associated processing circuitry 116 for processing, storing, and/or sending image data. Friction force may be used to stabilize the remote miniaturized examination device 100 during orienting and/or moving maneuvers, thus it is preferred to increase the static friction force at selected points such as near the ends of the remote miniaturized examination device by modifying the materials and/or texture and/or shape of the remote miniaturized examination device accordingly.

According to the first aspect of the present invention, in a second embodiment, the portable electromagnetically positioning system further comprises a portable external magnetic field generation assembly, which can generate pulsed magnetic fields respectively in three dimensions in a sequence, and the pulsed magnetic fields generated externally can be sensed by the first 3-dimensional magnetic field sensor.

FIGS. 7-10 provides four examples of portable external magnetic field generation assemblies. In the present invention, in one embodiment, magnetic field generation assemblies are excitation coil assemblies. In accordance with the aspects of the present invention, the three-dimensional excitation coil assembly have three perpendicularly placed coils, each winding around their own central axis and each central axis being perpendicular to two other axes, and three central axes intersecting at a center of the three-dimensional excitation coil assembly, wherein the three-dimensional excitation coil assembly is in a shape of a globe, or cubic.

The magnetic field generation assemblies are made of more than one excitation coils. Each excitation coil is characterized in coil length, coil radius, number of turns around an axis of the coil, and carrying current of the respective coil.

In the scope of the present invention, the three-dimensional excitation coil assembly consists of three individual excitation coils which can generate a magnetic field, the three magnetic fields generated in a timed-sequence are perpendicular to each other. Because the magnetic field generated is along the same direction of the magnetic axis of the excitation coil, as a result the three-dimensional excitation coil assembly which includes three coils, are perpendicular to each other. Three excitation coils are configured to have their geometrical centers coincide with each other. The shapes of the cross sections of each individual coil can be a disc or a square, rectangular, or ellipse or alike. There cross section areas of the three individual coils are slightly different, but the difference between any of the two should be less than 5%, so that the difference can be approximated to zero in the calculation model that descried as the second aspect of the present invention.

Within the scope of the present invention, the three-dimensional excitation coil assembly is designed according to the parameters and principles that are used in the calculation described afterwards. In the calculation, all the three-dimensional excitation coil is modeled as three perpendicular magnetic dipoles. Further, in one example, in considering the calculation model, the distance between the center of the three-dimensional excitation coil assembly and the remote object is at least 2.5 times longer than a geometry length of the three-dimensional excitation coil assembly, wherein the geometry length of the three-dimensional excitation coil assembly is the shortest of coil length. In another example, when the three-dimensional excitation coil assembly is spherical shaped, the calculation model is accurate when the distance between the three-dimensional excitation coil assembly and the remote object is longer than a cross sectional radius of the spherical three-dimensional excitation coil assembly, wherein the radius of the spherical shaped three-dimensional excitation coil assembly is the greatest radius of among three radii in the three-dimensional excitation coil assembly.

The magnetic moment is proportional to the number of turns, cross section area and the coil current. In the scope of the present invention, in one example, the coil length, coil radius, number of turns around an axis of the coil, and carrying current of the respective coil are the same, for the three coils, or substantially the same. In another example, they foregoing parameters are not to be exactly the same, or even under the situation that the parameters are believed to be the same, the number of the turns of coils are adjusted to make the magnetic moment of each coil with the same coil current are close to each other.

In one example of this embodiment, referring to FIG. 9, the excitation coil assembly is consisting essentially of three excitation coils, 701, 702 and 703. The coil 701 is continuously wounded around a magnetic coil axis y. The coil 702 is continuously wounded around a magnetic coil axis x. The coil 703 is continuously wounded around a magnetic coil axis a, with gradually increasing winding diameter from the top, one edge, to the middle, and with gradually decreasing winding diameter from middle to bottom edge, the other edge. The three magnetic axes x, y and z intersect at a point O, which is defined as a center of the excitation coil assembly. In this example, the three magnetic axis x, y and z are perpendicular to each other. In this example, the cross-section of each coil is a round shape. The cross-section diameter differs less than 5% with each other.

In another example of this embodiment, referring to FIG. 10, the excitation coil assembly is consisting essentially of three excitation coils, 801, 802 and 803. The coil 801 is continuously wounded around a magnetic coil axis y. The coil 802 is continuously wounded around a magnetic coil axis x. The coil 803 is continuously wounded around a magnetic coil axis a, with a uniform winding diameter from the top, one edge, to the middle, to bottom edge, the other edge. The three magnetic axes x, y and z intersect at a point O, which is defined as a center of the excitation coil assembly. In this example, the three magnetic axes x, y and z are perpendicular to each other. In this example, the cross-section of each coil is a round shape.

In still another example of this embodiment, referring to FIG. 11, the excitation coil assembly is consisting essentially of three excitation coils, 901, 902 and 903. The coil 901 is continuously wounded around a magnetic coil axis y. The coil 802 is continuously wounded around a magnetic coil axis x. The coil 903 is continuously wounded around a magnetic coil axis a, with a continuously increasing winding diameter from one end, having a first minimal diameter, to the middle, having a maximum diameter, to the other end, having a second minimal diameter. The three magnetic axes x, y and z intersect at a point O, which is defined as a center of the excitation coil assembly. In this example, the three magnetic axes x, y and z are perpendicular to each other. In this example, the cross-section of each coil is a round shape. In one instance, the three-dimension magnetic coil assembly in the globe configuration includes a winding of magnetic coils at 2 cm×4 cm×4 cm.

In yet another example of this embodiment, referring to FIG. 12, the excitation coil assembly is consisting essentially of three excitation coils, 1001, 1002 and 1003. The coil 1001 is continuously wounded around a magnetic coil axis y. The coil 1002 is continuously wounded around a magnetic coil axis x. The coil 1003 is continuously wounded around a magnetic coil axis a, with a uniform winding diameter from one end, having a first minimal diameter, to the middle, having a maximum diameter, to the other end, having a second minimal diameter. The three magnetic axes x, y and z intersect at a point O, which is defined as a center of the excitation coil assembly. In this example, the three magnetic axes x, y and z are perpendicular to each other. In this example, the cross-section of each coil is a circular, or rectangle, or square shape. In one instance, the three-dimension magnetic coil assembly in the rectangular configuration includes a winding of magnetic coils at 2 cm×4 cm×4 cm, in its three dimensions, as shown in FIG. 10. The three dimensions are x, y and z directions.

The sole purpose of the present invention is to determine the positon of the remote object, for that purpose, the magnetic field measurement period within one detection-measurement cycle needs to be accomplished within a confined time limit. On one hand, the confined time limit is firstly dictated by the movement frequency of the remote object. As one advantage of the present invention, is to detect the location of the remote object even though the remote object is not fixed in one location. On the other hand, the confined time limit is secondly dictated by the movement frequency of the excitation assembly itself. Even in situations that both the excitation assembly and remote object moves in a synchronized matter, due to the change in the ground magnetic field, in order for the location determination to be accurate, the detection-measurement cycle needs to be finished in the confined time limit. In accordance with the aspects of the present invention, each coil within the magnetic assembly can be individually charged. The individual coil needs to be charged in a precisely controlled timed sequence. Further the individual coil needs to be charged and discharged very quickly so that in each sequence there is no interference between the three magnetic fields generated.

The confined time limit is in turned further determined by additional factors including the acceptable detection accuracy. The acceptable detection accuracy is different for different applications and end use scenarios.

In one example, the remote object is a capsule endoscope with the magnetic sensor, which moves in a target area, for instance, a digest channel, at a rate of 10 mm/s. In order to achieve an acceptable position accuracy target of the 0.5 mm, the confined measurement time limit is set forth to be less than 50 ms.

In the scope of the present invention with respect to the magnetic sensor, which moves in a target area, for instance, a digest channel, at a rate of 10 mm/s. In order to achieve an acceptable position accuracy target of the 0.5 mm, the confined measurement time limit is set forth to be less than 50 ms.

Further, the time to charge and the time to discharge needs to be as short as possible. For example, less than 1 micro second is desired. The time duration to charge and discharge is decided the material composition of the coil, coil diameter and number of turns of the coils.

In the scope of the present invention, in one example the rectangular shaped three-dimensional magnetic coil assembly has a winding configuration of 4 cm×4 cm on one surface, with 1000 turns; 2 cm×4 cm on another surface, with 2000 turns. The excitation coils are selected are having a cross section with a diameter of 0.18 mm, resistivity at 160 Ohm or 240 ohm. In one instance, the current in the three-dimensional excitation coil assembly is 0.1 A. In another instance, among the three-dimensional excitation coil assembly, each coil has about 10 layers wound.

During the operation of the three-dimensional excitation coil assembly, excitation current is set at pulse 10 ms under voltage 24V, pulse constant current source 0.1 A. The current value can be set in real time program. The three-dimensional excitation coil assembly can deliver a maximum coil power of 7.2 W, detection times 2 times/sec, and the average power consumption <1 W.

For the purpose of the present invention, the external three-dimensional excitation coil assembly is to generate a magnetic field to be sensed by the first 3-dimensional magnetic field sensor inside miniaturized examination device, when the miniaturized examination device is deployed at the target location. Due to detection limit and sensitivity requirement of the 3-dimensional magnetic field sensor and specific distance configuration between the external three-dimensional excitation coil assembly and the target location, the three-dimensional excitation coil assembly is configured to generate a magnetic field, in some examples, at 0.02-12Gauss to be measured by the miniaturized examination device. In some other examples, the three-dimensional excitation coil assembly is configured to generate a magnetic field, at 0.005-1 Gauss, measured by the miniaturized examination device. In still some other examples, the three-dimensional excitation coil assembly is configured to generate a magnetic field, at 0.5-100 Gauss, measured by the miniaturized examination device. In still some other examples, the three-dimensional excitation coil assembly is configured to generate a magnetic field, at 10-2000 Gauss, measured by the miniaturized examination device.

Additionally, when the first 3-dimensional magnetic field sensor in the miniaturized examination device sensing the magnetic field generated by the external three-dimensional excitation coil assembly, the miniaturized examination device moves in the target location within a defined boundary. In another word, during operation or examination process, the distance between the 3-dimensional magnetic field sensor and external three-dimensional excitation coil assembly a relatively defined. In one example, the distance between the miniaturized examination device and the three-dimensional excitation coil assembly when it travels in the target location is between 3-5 cm. In another example, the distance between the miniaturized examination device and the three-dimensional excitation coil assembly when it travels in the target location is between 5-7 cm. In another example, the distance between the miniaturized examination device and the three-dimensional excitation coil assembly when it travels in the target location is between 7-11 cm. In another example, the distance between the miniaturized examination device and the three-dimensional excitation coil assembly when it travels in the target location is between 11-15 cm. In another example, the distance between the miniaturized examination device and the three-dimensional excitation coil assembly when it travels in the target location is between 15-20 cm.

Based on the value requirement magnetic field sensed by the 3D magnetic sensor in the miniaturized examination device, and distance constraint between the external three-dimensional excitation coil assembly and the 3D magnetic sensor, the three-dimensional excitation coil assembly is configured to generate magnetic moment in the range of 0.02-12 Gauss.

The three-dimensional excitation coil assembly further comprises a management module including an antenna to receive instruction from a communication unit, to turn on and off the excitation current and a timing protocol.

According to the first aspect of the present invention, in a third embodiment, additionally, the electromagnetically positioning system comprises an external reference position assembly. The external reference position assembly comprises a second 3-dimensional magnetic field sensor, configured to be placed on a support surface external to the isolated target remote area, as a reference magnetic field sensor. The second 3-dimensional magnetic field sensor, is placed at the external support surface with a predetermined location and fixed direction when the remote object travels inside the remote isolated target area. The placement of the second 3-dimensional magnetic field sensor can be used to reference if there is any movement of the external three-dimensional excitation coil and/or to reference the relative position and trace the movement of the remote object while traveling in the target area.

In accordance with the aspects of the present invention, any three-dimensional magnetic field sensor can be used to accomplish the purpose of the present invention. The three-dimensional magnetic field sensor can be selected from a group of sensors including a 3D magneto-resistive AMR sensor and 6-axis sensors. The appropriate sensor is chosen by considering detection range, sensitivity, noise, power consumption and sampling speed.

The external reference position assembly further comprises a control unit to read and send data and battery for power.

The reference 3D-magnetic field sensor(s) 104 needs to be aligned with the external excitation coil assembly in order to sense the x-, y-, and z-axis magnetic field. In this example, the z direction is along the reference position assembly axis. The magnetic field values sensed by the referenced 3D magnetic field sensor are preferably sent out using a wireless communication module included RF transmitter 106 and antenna 108.

During the operation, referring to FIG. 3, the external excitation coil assembly and reference position assembly are placed on a first and second surfaces of around and surrounding the target area, whereas the probe is placed in the target area in between the space, cavity, closed or semi-closed area in between the two surfaces. In one preferred example, the first surface and second surfaces of the surrounding the target areas are two opposing surfaces. Therefore, the system achieves most sensitivity of the generated magnetic field.

The fore-mentioned is one example of a particular implementation possible within the scope of the invention. The principles of the invention are not limited to this particular implementation and many variations are possible. It should be appreciated that many other variations in the details and arrangement of components may be made within the scope the invention.

In one example, referring to FIG. 3, the remote miniaturized device is a capsule, which can travel inside a patience's digestive track. Excitation coils are provided and placed on a belt, together with an antenna, the belt wraps around the patient in one turn. The peripheral length of the belt is about the waistline of an adult person. The three-dimensional magnetic assembly, including the excitation coils and antenna, is placed on a first position of the belt (abdomen position) of the patient. The reference position is placed on a second position, for example back of the patient near spin of the patient. This configuration can use the reference position to determine whether the belt has moves from its intended location or not during the position measurement period and provide calibration if needed. For example, tracing a distance between the capsule and reference position over time as a reference curve, and determining if the dislocation of the belt is significant and provide a calibration against the trace of the reference curve.

Referring to FIGS. 1 and 3, the three-magnetic excitation assembly is positioned on a belt across a person's body and the second magnetic sensor is secured on the same belt, with a distance away from the person's body. The distance, in this example, referring to FIG. 3, is ¼ of the peripheral of the belt. Additionally, the distance from the 3D magnetic sensor in the remote object to the second magnetic sensor is similar to the distance between the 3D magnetic sensor in the remote object to the three dimensional magnetic excitation assembly.

With the overview of the exemplary apparatus in mind, it should be understood that the determination of the position of the of a remote miniaturized examination device in real time having one three-dimension magnetic sensor in situ, and a reference position, is shown by the following equations and principles.

On a second aspect of the present invention, a method to use the three-dimensional magnetic excitation assembly to determine a position of the remote object is described and disclosed. The method comprises the following steps. First, determining three "pure" magnetic fields generated by three-dimensional magnetic excitation assembly; then, calculating the distance between three-dimensional magnetic excitation assembly and remote object; and calculating an orientation of the remote object after its position is calculated.

The first step of determining three "pure" magnetic fields generated by three-dimensional magnetic excitation assembly includes
determining an environmental magnetic field;
measuring the magnetic field generated by the three-dimensional magnetic field assembly;
removing the environmental magnetic field from the pulsed magnetic field measured to obtain pure magnetic field generated by the three-dimensional magnetic field assembly.

Wherein, the step of measuring the magnetic field generated by the three-dimensional magnetic excitation assembly comprising measuring the magnetic field by a pulsed sequence in a first, second and third coil in the three-dimensional magnetic excitation assembly. Further the first, second and third magnetic axis directions of each individual coil of the three-dimensional magnetic excitation assembly, and the first, second and third directions are perpendicular to each other.

Summary of Three Methods to Remove Environmental Magnetic Fields

Figure 13:
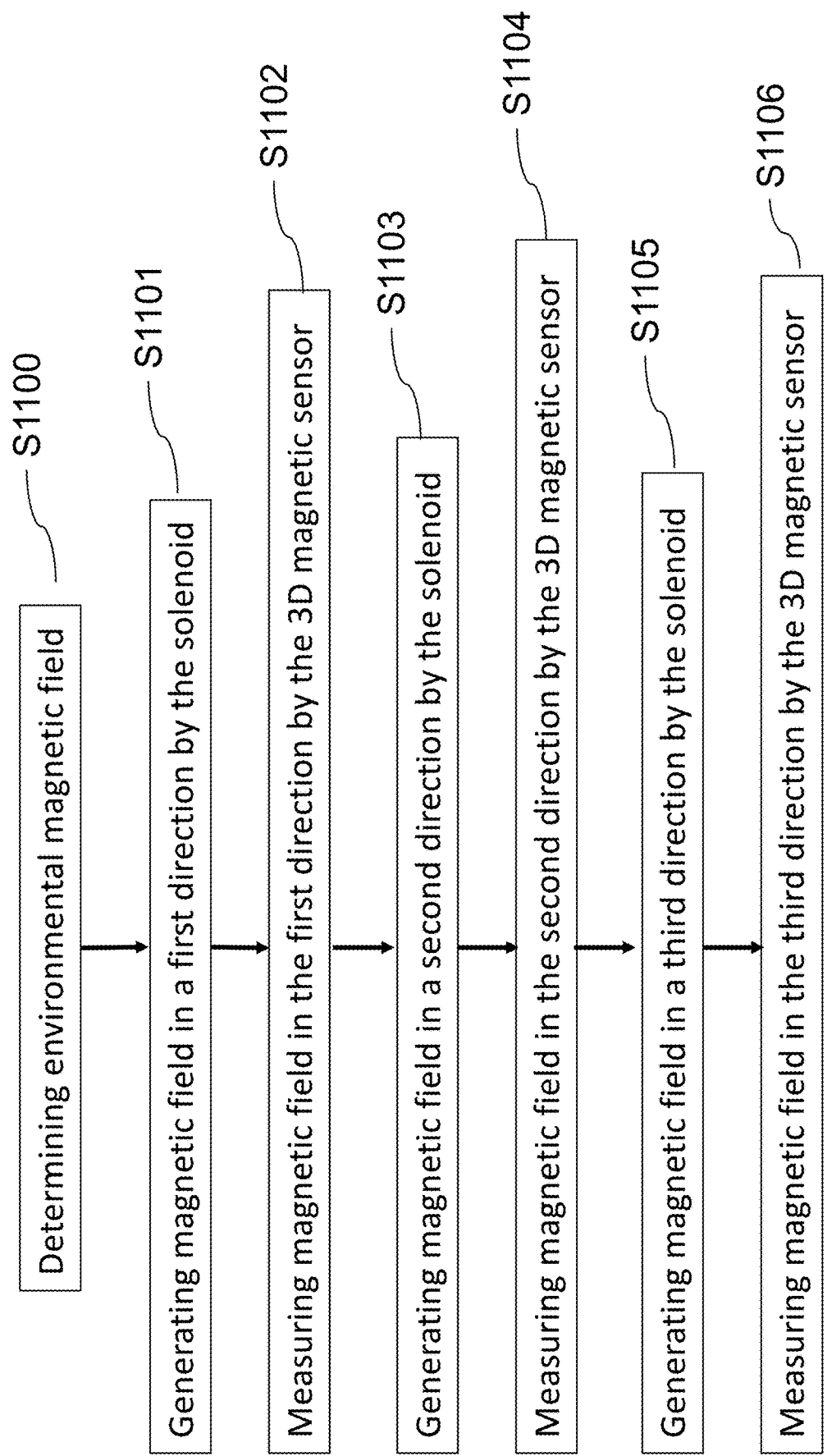
FIG. 13 is a process flow diagram showing the method steps to determine a position and an orientation of the remote object.
Figure 14:
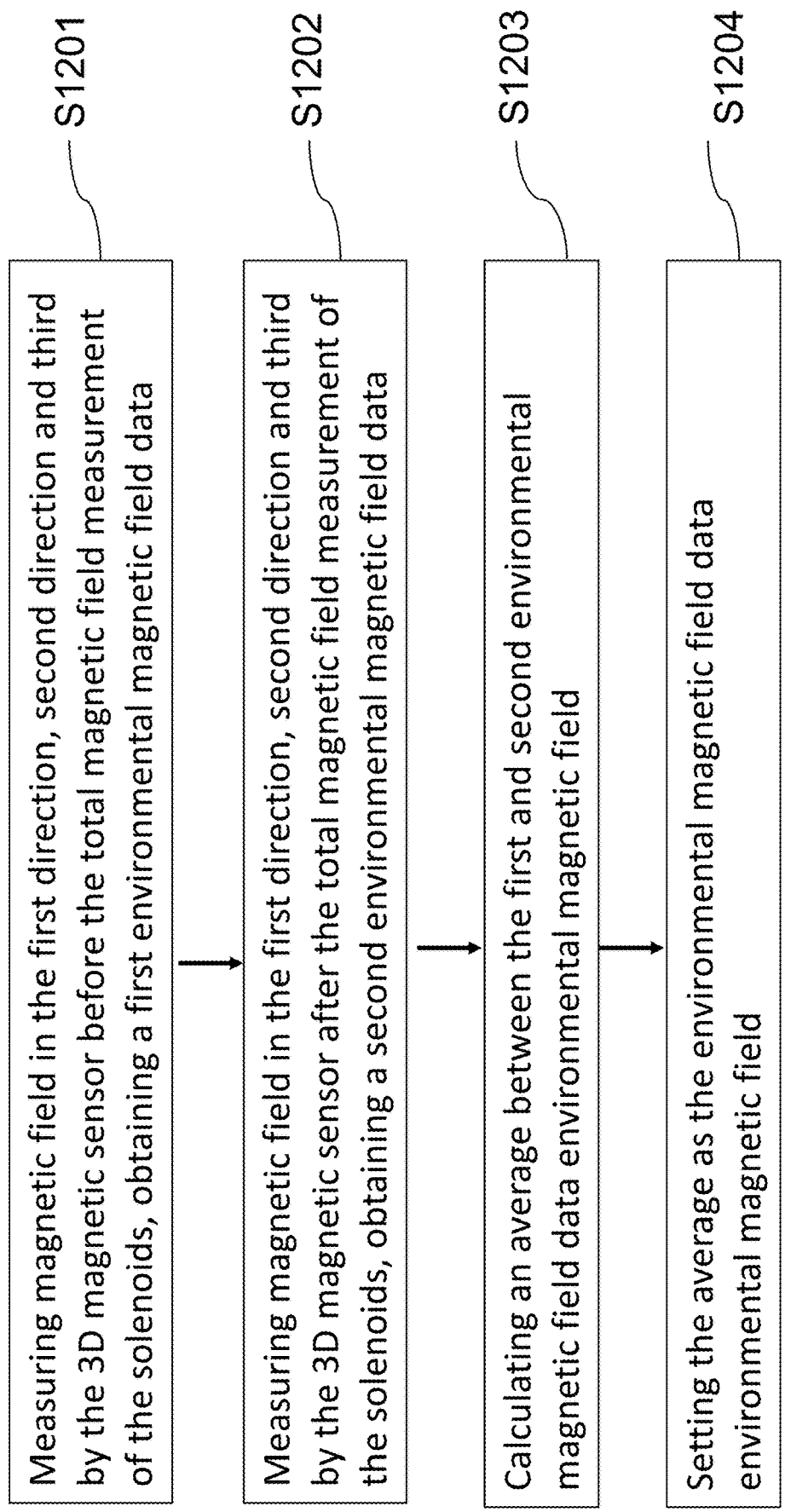
FIG. 14 is an exemplar process flow diagram illustrating the method steps to determining the environmental magnetic field.
Figure 15:
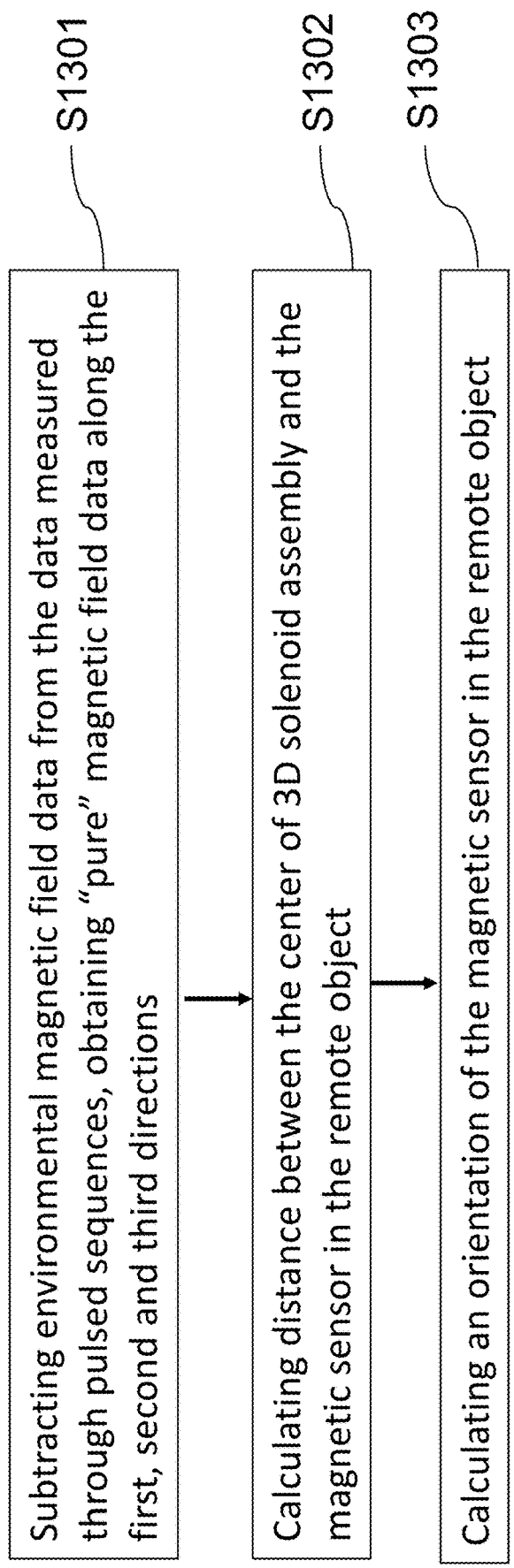
FIG. 15 is an exemplar process flow diagram illustrating the method steps to obtaining the position and orientation of the remote object, in accordance with the aspects with the present invention.
Figure 16:
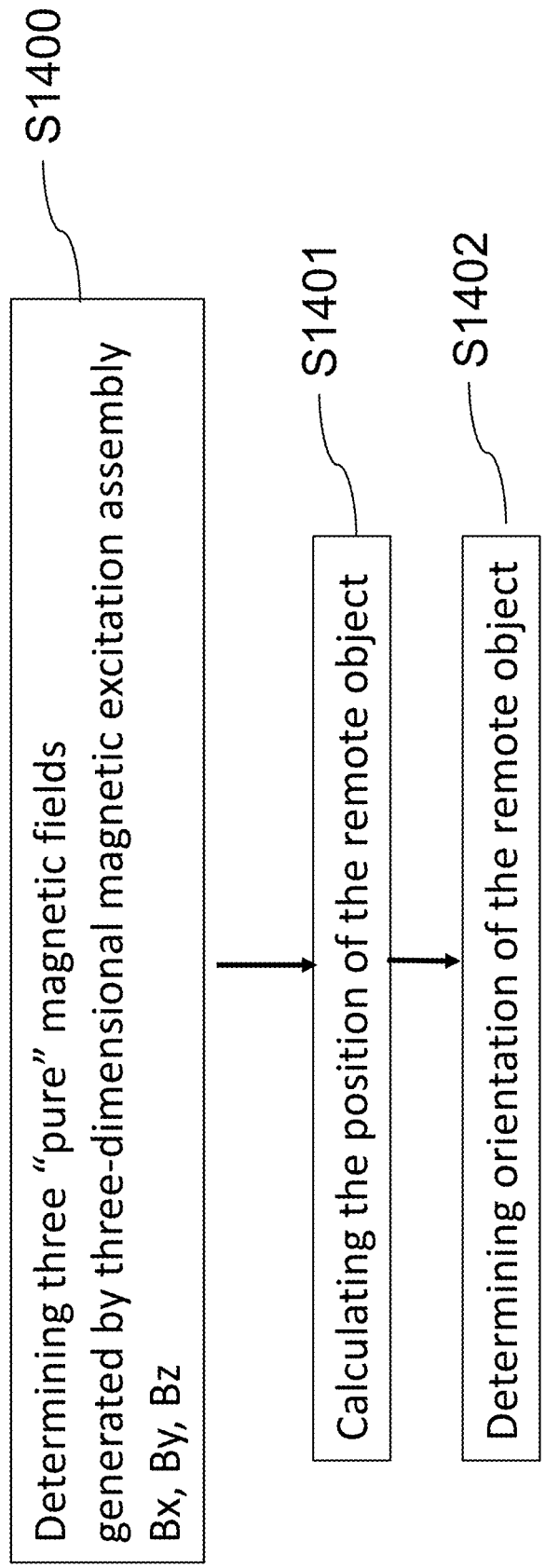
FIG. 16 is an exemplar process flow diagram illustrating the method steps to obtaining the position and orientation of the remote object, in accordance with the aspects with the present invention.
Figure 17:
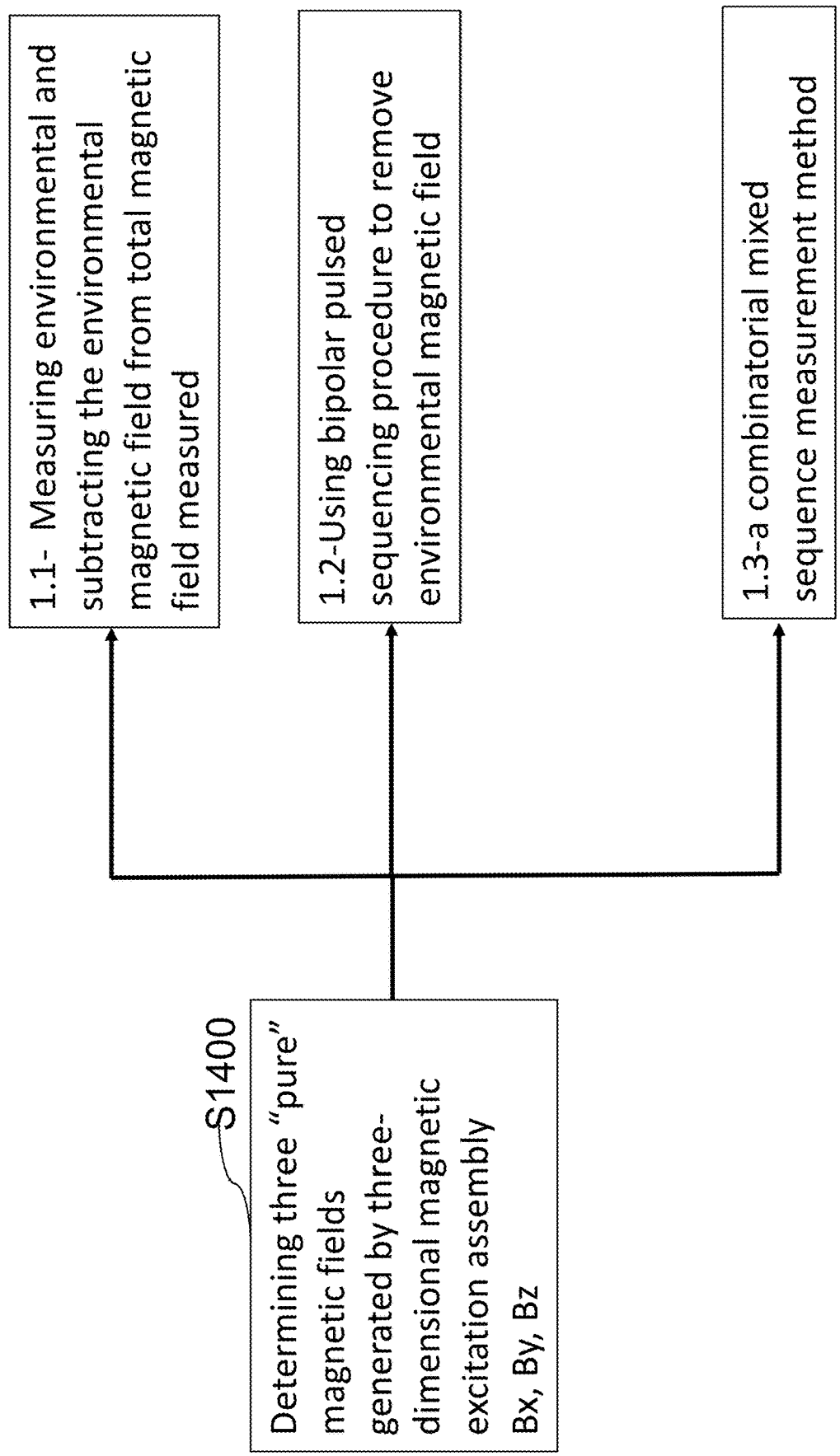
FIG. 17 illustrate three alternative pathways to obtain three "pure" magnetic fields generated by three-dimensional magnetic excitation assembly.

There are three alternative methods to determine three "pure" magnetic fields generated by three-dimensional magnetic excitation assembly as disclosed herein. A first method involves measuring the environmental magnetic field data and removing the environmental magnetic field data from the measured total magnetic field data of the three-dimensional magnetic assembly. According to this first method, detail sequence of steps is listed in FIGS. 13 and 14. The distinction between the method steps are in when to take the environmental magnetic field measurement and if an average of the before/after the actual total magnetic fields generated by three-dimensional magnetic excitation assembly is used in a subsequent calculation. The two method steps listed in FIGS. 13 and 14 can be chosen according to the specific measurement conditions. If the environmental magnetic field changes a lot before and after the total magnetic field data measurement, method steps listed in FIG. 14 is more appropriate in order to obtain most accurate result.

A second method involves measuring total magnetic field data using a bipolar pulsed sequencing method, wherein the environmental magnetic field data is to be measured in a positive and negative direction, and the addition results of the two total magnetic field data lead to cancellation of the environmental magnetic field.

A third method involves using a combinatorial sequencing method to measure the total magnetic fields three times, and among which at least one electrical current direction for one of the coil is different from the previous sequence.

Detail Explanation of Each Alternative Steps of Determining Three "Pure" Magnetic Fields Generated by Three-Dimensional Magnetic Excitation Assembly Using the First Method The three-dimensional magnetic excitation assembly disclosed herein is intended to be placed and used under an environmental magnetic field on earth. The influence of the earth magnetic field must be considered in the measurement and removed from the calculation in positon determination of the remote object.

Although the earth magnetic field has little change with time, but the ferrite materials in the environment may change the local earth magnetic field differently at different location. the most important is that magnetic sensor orientation may change while moving thus the three magnetic field components of the magnetic field vector may change with time. It is the best that the environmental magnetic field is determined around the same time when the position determination is performed.

In one instance, the remote object is a capsule endoscope. When a person wears a 3-dimensional excitation coil assembly and takes a capsule endoscope fixed with a magnetic sensor, when he or she moves, the measured environmental magnetic field may change. Even the environmental magnetic field doesn't change, the orientation of the magnetic sensor may change when it rotates when the body rotates, thus the reading of the components of the 3D magnetic field by the magnetic sensor will change. So that the environment magnetic field should be measured vicinity to the position determination is made.

In one example, the environmental magnetic field is measured just before the application of pulsed magnetic field for position determination of the remote object, and the measured valued is set forth as the value of the environmental magnetic field and deducted in the subsequent calculations.

In another example, the environmental magnetic field is measured just after the application of pulsed magnetic field for position determination of the remote object, and the measured valued is set forth as the value of the environmental magnetic field and deducted in the subsequent calculations.

In a preferred example, the environmental magnetic field is measured both before and after the application of pulsed magnetic field for position determination of the remote object and then the average of the two measured-data is taken as the value of the environmental magnetic field and deducted in the subsequent calculations. FIGS. 13 and 14, illustrated two embodiments of method steps of the present invention. In a first embodiment, the environmental magnetic field is first determined and the magnetic field generated by the three-dimensional excitation coil assembly is measured one by one in a pre-determined sequence.

In one embodiment of the present invention, the three-dimensional magnetic excitation assembly and the remote object are placed on earth. The environmental magnetic field is substantially the earth magnetic field. When the magnetic field generated by the coil current is weaker than the earth magnetic field, the orientation change of the magnetic sensor can bring a considerable error, for instance, 1 degree of the sensor orientation change can cause an error up to 1.6% of total earth magnetic field. For example, when the total measurement period is 50 ms, the movement of the remote object shall be limited to less than 20 degrees per second or 3.3 rpm for 1 degree orientation change. Further actions taken by the users, like faster turning or moving suddenly, either planned or unavoidably, will cause higher location measurement error, therefore the second method has advantage to over the first method under these conditions.

The preferred exemplar method includes the steps of measuring the Earth magnetic field both before and after the pulsed sequence measurement and then taking an average can greatly reduce the type of error caused by orientation change of the remote object. Within the first method, preferred exemplar method, there are also more than two operation procedures.

In a first preferred operation procedure, first measuring magnetic field in the first direction, second direction and third by the 3D magnetic sensor in the remote object before the pulsed sequence by the solenoids, obtaining a first environmental magnetic field data;
generating magnetic field in a first direction by the solenoid under a first timed sequence;

generating magnetic field in a second direction by the solenoid under a second timed sequence;

generating magnetic field in a third direction by the solenoid under a third timed sequence;

measuring magnetic field in the first direction, second direction and third direction by the 3D magnetic sensor in the remote object after the pulsed sequence by the solenoids, obtaining a second environmental magnetic field data; and taking the average data between first and second environmental magnetic field data as the environmental magnetic field value to be deducted from the measured magnetic field data.

In a second preferred operation procedure, the Earth magnetic field measurement and measurement of the magnetic field generated by the solenoid is interspersed in to the overall position measurement sequence. By being interspersed, it means, the measurement for environmental magnetic field occurs at least one time in between the pulsed sequence generated by the three-dimensional magnetic excitation assembly, not just before or after the pulsed sequence of the three-dimensional magnetic excitation assembly. In one example, the entire measurement process includes the following steps. Within this preferred operation procedure of the second method, each earth measurement can be on one direction or on three directions. One example of measurement sequence is described below.

First, measuring the environmental magnetic field in the first direction, second direction and third direction by the 3D magnetic sensor in the remote object before the pulsed sequence by the solenoids, obtaining a first environmental magnetic field data; followed by performing a first solenoid pulse magnetic field measurement along a first direction;

Second, measuring the second environmental magnetic field by the 3D magnetic sensor in the remote object, obtaining a second environmental magnetic field data, followed by performing a second solenoid pulse magnetic field measurement along a second direction;

Third, measuring the third environmental magnetic field by the 3D magnetic sensor in the remote object, obtaining a third environmental magnetic field data, followed by performing a third solenoid pulse magnetic field measurement along a third direction;

Fourth, optionally, measuring the environmental magnetic field in the first, second and third direction by the 3D magnetic sensor in the remote object, obtaining a fourth environmental magnetic field data.

Further, when the environmental magnetic field is substantially the Earth magnetic field, the measurement of environmental magnetic field can not only help to determine the pure the magnetic field generated by the three-dimensional excitation assembly, but also provide indication if and how much the remote object moves or has moved with respect to its previous position. If the movement of the remote object is more than a preset threshold value, then position measurement frequency needs to be increased, or the time duration for one cycle of position measurement needs to be reduced in order to maintain the precision target. Since the time it takes to measure Earth magnetic field is about 10 microseconds, the most effective way to reduce the measurement cycle time is to speed up the pulsed sequencing steps of solenoids.

For example, when there is one direction of Earth magnetic field measured by the 3D sensor in the remote object before and after the pulsed sequence of solenoids is more than 2% of the Earth magnetic field or 10 m Gauss, the movement of the remote object is considered to be too quickly and the measurement speed shall be increased in order to maintain accurate position determination target. Under this situation, for example when the change in Earth magnetic field measured by the 3D magnetic sensor in the remote object is 20 m Gauss, instead of a threshold value of 10 ms to finish a 3D magnetic field measurement by the magnetic sensor, the measuring time need to be reduced to 5 ms. Consequently, the excitation coil current pulse period shall be also reduced to slightly longer (e.g., 5.5 ms) than 5 ms from 10 ms. At the same time, the measurement will surfer a trade off in sensitivity due to increase in noise of the 3D magnetic sensor of the remote object. In a system, where the structure of three-dimensional excitation assembly and 3D magnetic sensor is fixed, a predefined optimum pulse sequence including pulsed width and magnitude, and measuring time can be chosen to balance the measurement target for position precision and tolerance for error in sensitivity. The predefined optimum pulse sequence can be implemented to adopt a preset empirical value, or to be adaptively changed by monitoring the change of earth field component during each measurement. Therefore, optionally, the method disclosed herein further comprises a step to determining the change in position of the remote object from its previous position within the same measurement cycle, if the absolute value of change in position is greater than a first threshold value, the cycle time or a time duration in pulsed sequencing step will be adjusted accordingly.

Using the Second Method-Bipolar Pulsed Sequencing Step to Remove Environmental Magnetic Field Regarding the step of removing environmental magnetic field, in the second alternative method embodiment, the environmental magnetic field does not need to be separately determined before it is removed. Instead, a bipolar pulsed sequencing steps in measuring the total magnetic field can be utilized to effectively cancel out the environmental magnetic field effect. The bipolar pulsed sequencing, as the name indicates, referring to FIGS. 7 and 8, for any given x, y and z direction of any coil, a positive current is applied and immediately followed by a negative current or vice versa.

However, in order for the bipolar pulsed sequencing method to work well, to meet position precision and sensitive requirement, the remote object should not move with a certain predefined range and/or the three components (x, y and z components) of the environment magnetic field measured under the positive and negative current conditions need to be fairly consistent with each other along each direction of measurement during each pulsed current measurement. This second alternative method to remove the environmental magnetic field is not as versatile as the first method, especially when both the three-dimensional magnetic excitation assembly and remote object may move during the entire position measurement cycle, in both planned or unexpected manners.

In the present invention, two operation procedures within this bipolar method are disclosed and described in FIGS. 7 and 8. In the exemplar pulsed sequences, each pulse lasts for 10 ms, the rising edge and the falling edge are programmed to be less than 1 ms. The excitation coils are pulsed at +x, −x, +y, −y, +z and −z directions, sequentially or not sequentially.

FIG. 7 illustrates a first operation procedure. FIG. 7 shows two exemplar pulsed sequences to charge the excitation coil to measure respective generated magnetic field in each coordinated direction, for each individual excitation coil.

In a first example of the pulse sequence, the excitation coil is charged in the x, y, z direction only in the positive direction, sequentially for 10 ms each.

A detailed first operation procedure can be the following. 1) a first magnetic coil is applied a current in the positive amplitude direction for 10 ms, 2) then a second magnetic coil is applied the same current in the positive amplitude direction for 10 ms, and 3) then a third magnetic coil is applied the same current in the positive amplitude direction for 10 ms. Immediately, 4) the first magnetic coil is applied a current in the negative amplitude direction for 10 ms, 5) then the second magnetic coil is applied the same current in the negative amplitude direction for 10 ms, and 6) then the third magnetic coil is applied the same current in the negative amplitude direction for 10 ms.

FIG. 8 illustrates a second operation procedure. In the second example of the pulse sequence, the excitation coil is charged in the x, y, z direction, both positively and negatively, sequentially for 10 ms each. Therefore, every measurement last for 60 ms. Such measurement is repeated every 0.5 s.

In the second operation procedure, 1) a first magnetic coil is applied a current in the positive amplitude direction for 10 ms, then 2) the first magnetic coil is applied the same current in the negative amplitude direction for 10 ms; 3) a second magnetic coil is applied the same current in the positive amplitude direction for 10 ms, then 4) the second magnetic coil is applied a current in the negative amplitude direction for 10 ms; 5) the third magnetic coil is applied the same current in the positive amplitude direction for 10 ms, and 6) then the third magnetic coil is applied the same current in the negative amplitude direction for 10 ms.

After the application of either operation procedure to the coil assembly, the following nine calculations are performed. In this example, a ground magnetic field is measured every time before each examination. Further, three magnetic coils X, Y, and Z are charged individually in three component coordinated directions (x, y, and z) using one of the two operation procedures in the bipolar method respectively. Then the environmental magnetic field is subtracted from the results. Descriptive equations are the following.

$$B_{X_x}=(B_{X_+}(x)-B_{X_-}(x))/2$$

$$Bx_y=(B_{X_+}(y)-B_{X_-}(y))/2$$

$$Bx_z=(B_{X_+}(z)-B_{X_-}(z))/2$$

$$By_x=(B_{Y_+}(x)-B_{Y_-}(x))/2$$

$$By_y=(B_{Y_+}(y)-B_{Y_-}(y))/2$$

$$By_z=(B_{Y_+}(z)-B_{Y_-}(z))/2$$

$$Bz_x=(B_{Z_+}(x)-B_{Z_-}(x))/2$$

$$Bz_y=(B_{Z_+}(y)-B_{Z_-}(y))/2$$

$$B_{Z_z}=(B_{Z_+}(z)-B_{Z_-}(z))/2 \quad (30)$$

After the application In each individual equation, the environmental magnetic field is successfully removed in the calculation. Each individual calculation of above 9 equations Results in a component magnetic field, which will in turn to be used to calculate a Bx, By and Bz of the solenoid.

In the above equations, each symbol are described below.

$B_{X_x}$ is the magnetic field of the X coil along x component direction after the excitation, being measured by the 3D sensor of including the environmental magnetic field.

$B_{X_y}$ is the magnetic field of the X coil along y component direction after the excitation.

$B_{X_z}$ is the magnetic field of the X coil along z component direction after the excitation.

$By_x$ is the magnetic field of the Y coil along x component direction after the excitation.

$By_y$ is the magnetic field of the Y coil along y component direction after the excitation.

$By_z$ is the magnetic field of the Y coil along z component direction after the excitation.

$Bz_x$ is the magnetic field of the Z coil along x component direction after the excitation.

$Bz_y$ is the magnetic field of the Z coil along y component direction after the excitation.

$Bz_z$ is the magnetic field of the Z coil along z component direction after the excitation.

$B_{X+}(x)$ means the magnetic field of the X coil along x component direction after applying positive amplitude of electrical current.

$B_{X-}(x)$ means the magnetic field of the X coil along x component direction after applying negative amplitude of electrical current.

$B_{X+}(y)$ means the magnetic field of the X coil along y component direction after applying positive amplitude of electrical current.

$B_{X-}(y)$ means the magnetic field of the X coil along y component direction after applying negative amplitude of electrical current.

$B_{X+}(z)$ means the magnetic field of the X coil along z component direction after applying positive amplitude of electrical current.

$B_{X-}(z)$ means the magnetic field of the X coil along z component direction after applying negative amplitude of electrical current.

$By_+(x)$ means the magnetic field of the Y coil along x component direction after applying positive amplitude of electrical current.

$By_-(x)$ means the magnetic field of the Y coil along x component direction after applying negative amplitude of electrical current.

$By_+(y)$ means the magnetic field of the Y coil along y component direction after applying positive amplitude of electrical current.

$By_-(y)$ means the magnetic field of the Y coil along y component direction after applying negative amplitude of electrical current.

$By_+(z)$ means the magnetic field of the Y coil along z component direction after applying positive amplitude of electrical current.

$By_-(z)$ means the magnetic field of the Y coil along z component direction after applying negative amplitude of electrical current.

$Bz_+(x)$ means the magnetic field of the Z coil along x component direction after applying positive amplitude of electrical current.

$Bz_-(x)$ means the magnetic field of the Z coil along x component direction after applying negative amplitude of electrical current.

$Bz_+(y)$ means the magnetic field of the Z coil along y component direction after applying positive amplitude of electrical current.

$Bz_-(y)$ means the magnetic field of the Z coil along y component direction after applying negative amplitude of electrical current.

$Bz_+(z)$ means the magnetic field of the Z coil along z component direction after applying positive amplitude of electrical current.

Bz_(z) means the magnetic field of the Z coil along z component direction after applying negative amplitude of electrical current.

Using the Third Method-Combinatorial Mixed Sequencing Method to Remove Environmental Magnetic Field In the system described in FIG. 2 of the present disclosure, when more than one solenoid are used, a third method becomes available to remove environmental magnetic field.

The Combinatorial mixed sequencing method includes three solenoid are provided electrical current at the same time, for three times. Among which, at least one electrical current has a different current direction from the previous current. Measuring the magnetic field generated for three times, combinations, assuming the environmental magnetic field stays the same during the entire measurement period and only electrical current changes directions. In the method naming nomenclature, combinatorial means there are more than one combination. "Mixed sequencing" means that the direction of the current can have mixed positive and negative directions in one combination. Herein, combination means in one operation procedure, one constituent coil (X, Y and Z) of each solenoid are all excited at the same time. The detail operations of the procedures can be understood by the following explanation.

For one solenoid having coils X, Y and Z, each with magnetic moments Mx, My, and Mz, the following relationship can be established: Mx:My:Mz=mx:my:1. When applying pulsed magnetic excitation to three solenoids in one system at the same time, for example, three measuring conditions can be (Mx, My, Mz), (−Mx, My, Mz) and (−Mx, −My, Mz) can be established. The x, y z directions for a solenoid are illustrated in FIGS. 9-11. The pulsed current is illustrated in FIG. 7.

For combination 1 (Mx, My, Mz)

$$Bx'_x + By'_x + Bz'_x = B1'_x$$

$$Bx'_y + By'_y + Bz'_y = B1'_y$$

$$Bx'_z + By'_z + Bz'_z = B1'_z \tag{8}$$

Wherein, B1' is for the first combination. $B1'_x$ is for the magnetic field of a first solenoid along x component direction. $B1'_y$ is for the magnetic field of the solenoid along y component direction. $B1'_z$ is for the magnetic field of the solenoid along z component direction.

For combination 2 (−Mx, My, Mz)

$$-Bx'_x + By'_x + Bz'_x = B2'_x$$

$$-Bx'_y + By'_y + Bz'_y = B2'_y$$

$$-Bx'_z + By'_z + Bz'_z = B2'_z \tag{9}$$

Wherein, B2' is for the second combination.
$B2'_x$ is for the magnetic field of the solenoid along x component direction.
$B2'_y$ is for the magnetic field of the solenoid along y component direction.
$B2'_z$ is for the magnetic field of the solenoid along z component direction.

For combination 3 (−Mx, −My, Mz)

$$-Bx'_x - By'_x + Bz'_x = B3'_x$$

$$-Bx'_y - By'_y + Bz'_y = B3'_{y-}$$

$$-Bx'_z - By'_z + Bz'_z = B3'_z \tag{10}$$

Wherein, B3' is for the third combination.
$B3'_x$ is for the magnetic field of the solenoid along x component direction.
$B3'_{y-}$ is for the magnetic field of the solenoid along y-component direction.
$B3'_z$ is for the magnetic field of the solenoid along z component direction.

In the above equations' groups, the symbol meanings are described below.
$Bx'_x$ is for magnetic field generated by the excitation coil X along x component direction.
$By'_x$ is for magnetic field generated by the excitation coil Y along y component direction.
$Bz'_z$ is for magnetic field generated by the excitation coil Z along z component direction.
$By'_x$ is for magnetic field generated by the excitation coil X along x component direction.
$By'_y$ is for magnetic field generated by the excitation coil Y along y component direction.
$By'_z$ is for magnetic field generated by the excitation coil Z along z component direction.
$Bz'_x$ is for magnetic field generated by the excitation coil X along x component direction.
$Bz'_y$ is for magnetic field generated by the excitation coil Y along y component direction.
$Bz'_z$ is for magnetic field generated by the excitation coil Z along z component direction.
' in the equation groups 8, 9 and 10 are to indicate the symbol is established and characterized in the 3D coordinates associated with the remote object.

Combining the solenoids magnetic field listed above, the magnetic field of each solenoid can be derived as $$Bx'_x = (B1'_x - B2'_x)/2 \; By'_x = (B2'_x - B3'_x)/2 \; Bz'_x = (B1'_x + B3'_x)/2$$

$$Bx'_y = (B1'_y - B2'_y)/2 \; By'_y = (B2'_y - B3'_y)/2 \; Bz'_y = (B1'_y + B3'_y)/2$$

$$Bx'_z = (B1'_z - B2'_z)/2 \; By'_z = (B2'_z - B3'_z)/2 \; Bz'_z = (B1'_z + B3'_z)/2 \tag{11}$$

Once the nine component magnetic fields (3 x, y and z component magnetic field for each solenoid and there are a total of three solenoids), are determined, by using formula (3)-(5) below, the Bx, By and Bz, can be derived. In this calculation, mx, my are known parameters based on system design.

This third method described above teaches an effective way to remove environmental magnetic field without actual measurement of the environmental magnetic field. As it has been disclosed in the corresponding system description, when using three solenoids, the precision for position detection and detection limit are increased for a fixed coil setup having a maximum allowable current and fixed wire diameter. When pulsed current is generated in the three solenoids at the same time, it is increased overall power output limit and, in a way, "overcome" the power supply limit. The above equation groups (8), (9) and (10) offers three examples to make combination 1, combination 2 and combine 3. In principle, a combination of the two different directions (positive and negative) of the current in each excitation coil can be constructed and there are a total of $2^3=8$ combinations can be built.

Calculating the Position of the Remote Object Based on Formula (1)

The fundamental principal for the calculations is based on that the generated magnetic field by the excitation coil assembly can be accurately detected. When the distance between the excitation coil assembly and 3D magnetic sensor is far greater than dimension of the excitation coil assembly, then the magnetic field generated by the excitation coil assembly can be assumed to be equivalent to be generated by a permanent magnetic dipole.

After we get the three "pure" coil magnetic fields generated by the pulse currents of the 3D solenoid assembly, the distance between the three-dimensional magnetic excitation assembly and the remote object is calculated by the following formula (1), wherein the three-dimensional magnetic excitation assembly and the remote object is defined by a distance from the center of the three-dimensional magnetic excitation assembly to the center of the 3D magnetic sensor in the remote object.

$$p = A^{1/3} / [(Bx^2 + By^2 + Bz^2)/6]^{1/6} \quad (1)$$

Wherein p is the distance between center of the three-dimensional magnetic excitation assembly to the center of the 3D magnetic sensor in the remote object. A is $$A = \frac{\mu_0}{4\pi} |\vec{M}|$$

$\mu_0$ is the vacuum magnetic permeability, M is a magnetic moment of an individual excitation coil, which is proportional to the total number of coil turns N, coil current I and coil cross section S. Further, M, N and I have the following relationship:

$$M \propto N \cdot I \cdot S$$

In formula (1) it is assumed that the magnetic moment of each coil in the three-dimensional magnetic assembly is equal to M.

Bx is the total coil magnetic field of the coil along x direction coil. By is the total coil magnetic field of the coil along y direction. Bz is the total coil magnetic field of the coil along z direction. The x, y z directions are magnetic axes of the three-dimensional excitation coil assembly. Exemplary x, y and z directions or axes are illustrated in FIGS. 7-10. Bx can calculated by three component magnetic field as shown in formula (2).

$$Bx^2 = Bx'^2_x + Bx'^2_y + Bx'^2_z \quad (2)$$

$Bx'_x$, $Bx'_y$, $Bx'_z$ are the three components of magnetic field measured by the 3D magnetic sensor.

Correspondingly, By and Bz are the total magnetic field of the same coil in y and z directions, each are also contributed by three components magnetic fields measured by the 3D magnetic sensor in the remote object respectively.

$$By^2 = By'^2_x + By'^2_y + By'^2_z \quad (3)$$

$$Bz^2 = Bz'^2_x + Bz'^2_y + Bz'^2_z \quad (4)$$

Figure 6:
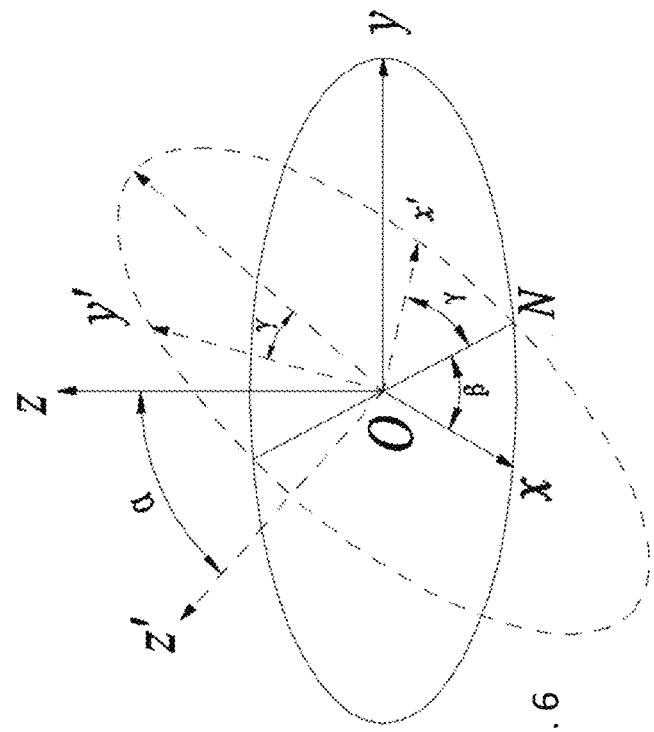
FIG. 6 is an illustration of a spatial relationship between the center of the three-dimensional excitation coil assembly to the position the remote object, wherein position O is the center of the three-dimensional excitation coil assembly.

Referring to FIG. 6, for calculation purpose, the position of 3D solenoid assembly object in 3-dimensional coordinates is P (a, b, c) for the x, y, z coordination respectively, and they meet the following requirements in formula (5).

$$a = \pm p \sqrt{(Bx^2 p^6 / A^2 - 1)/3}$$

$$b = \pm p \sqrt{(By^2 p^6 / A^2 - 1)/3}$$

$$c = \pm p \sqrt{(Bz^2 p^6 / A^2 - 1)/3} \quad (5)$$

Bx, By and Bz, p and A carry the same meaning as in formulas (1)-(4). According to the above formulas (1)-(5), eight combination of the result can be derived, among which, only one data point would be meaningful as considering system restriction and the continuity from the last calculated location.

Calculating the Distance P Using Formula (6)

Alternatively, for a system having more than one solenoid as described above, if the magnetic moments of the three solenoids in the 3D solenoid assembly, we can calculate the distance by the modification of formula (1). The fundamental principal for the calculations are based on that the generated magnetic field by the excitation coil assembly can be accurately detected. When the distance between the excitation coil assembly and 3D magnetic sensor is far greater than dimension of the excitation coil assembly, then the magnetic field generated by the excitation coil assembly can be assumed to be equivalent to be generated by a permanent magnetic dipole. When the magnetic moment of the excitation coil Mx, My and Mz, they have the following relationship: Mx:My:Mz=mx:my:1.

And Mz=M, then equation 1 is changed to the following equation (6)

$$p = A^{1/3} / [((Bx/mx)^2 + (By/my)^2 + Bz^2)/6]^{1/6}$$

$$p = A^{1/3} / [((Bx/mx)^2 + (By/my)^2 + Bz^2)/6]^{-1/6} \quad (6)$$

Wherein p, A and Bx, By, Bz carry the same meaning as in formula (1).

Consequently, equations in formula (5) regarding the location in 3D coordination of 3D solenoid assembly are modified to formula group (7)

$$a = \pm p \sqrt{((Bx/mx)^2 p^6 / A^2 - 1)/3}$$

$$b = \pm p \sqrt{((By/my)^2 p^6 / A^2 - 1)/3}$$

$$c = \pm p \sqrt{(Bz^2 p^6 / A^2 - 1)/3} \quad (7)$$

Determining Orientation of the Remote Object

After the position of the remote object is determined, the orientation of can be determined using the following steps. In the scope of the present invention, determination of the orientation of the remote object means determining rotation angles of the remote object with respect to its magnetic axes. Further, the rotation angles of the remote object are defined as the same as and represented by the rotation angles of 3D magnetic sensor in the remote object. The rotation angles of 3D magnetic sensors are defined with respect to three magnetic axes x', y', and z'.

First, we will calculate magnetic field of each citation coil (Bx, By and Bz) in the 3D solenoid assembly coordination. The calculation is based on the magnetic dipole model.

$$Bx = \frac{3\mu_0}{8\pi} \frac{M}{r^3} \sin 2\varphi \cos\theta \quad (12)$$

$$By = \frac{3\mu_0}{8\pi} \frac{M}{r^3} \sin 2\varphi \sin\theta$$

$$Bz = \frac{\mu_0}{2\pi} \frac{M}{r^3} \left(1 - \frac{3}{2}\sin^2\varphi\right)$$

For the three excitation coils (X, Y and Z), we calculate the location in the 3D solenoid assembly coordination as the following as components, along each x, y, z directions.

$$Bx_x = \frac{\mu_0}{4\pi} \frac{Mx(2a^2 - b^2 - c^2)}{(a^2 + b^2 + c^2)^{5/2}}$$ (13)

$$Bx_y = \frac{3\mu_0}{4\pi} \frac{Mx \cdot a \cdot b}{(a^2 + b^2 + c^2)^{5/2}}$$

$$Bx_z = \frac{3\mu_0}{4\pi} \frac{Mx \cdot a \cdot c}{(a^2 + b^2 + c^2)^{5/2}}$$

$$By_x = \frac{3\mu_0}{4\pi} \frac{My \cdot a \cdot b}{(a^2 + b^2 + c^2)^{5/2}}$$ (14)

$$By_y = \frac{\mu_0}{4\pi} \frac{My(2b^2 - a^2 - c^2)}{(a^2 + b^2 + c^2)^{5/2}}$$

$$By_z = \frac{3\mu_0}{4\pi} \frac{My \cdot b \cdot c}{(a^2 + b^2 + c^2)^{5/2}}$$

$$Bz_x = \frac{3\mu_0}{4\pi} \frac{Mz \cdot a \cdot c}{(a^2 + b^2 + c^2)^{5/2}}$$ (15)

$$Bz_y = \frac{3\mu_0}{4\pi} \frac{Mz \cdot b \cdot c}{(a^2 + b^2 + c^2)^{5/2}}$$

$$Bz_z = \frac{\mu_0}{4\pi} \frac{Mz(2c^2 - a^2 - b^2)}{(a^2 + b^2 + c^2)^{5/2}}$$

Wherein the magnetic field are ($Bx_x$, $Bx_y$, $Bx_z$), ($By_x$, $By_y$, $By_z$), ($Bz_x$, $Bz_y$, $Bz_z$). The corresponding measurement of the magnetic sensor for the three excitation coils X, Y, and Z are $$(Bx'_x, Bx'_y, Bx'_z)(By'_x, By'_y, By'_z)(Bz'_x, Bz'_y, Bz'_z)$$

If there is no rotation of the magnetic sensor in the 3D solenoid assembly coordination, the defined x, y, z axes in magnetic coil excitation assembly and x', y', z,' axes measured by magnetic sensor in the remote object, are parallel to each other respectively along the same direction. However, if there is a rotation, axes measured by magnetic sensor in the remote object and the axes in the magnetic coil excitation assembly establish relationships with rotation matrix. For example, axis z' and axis z has the following relationship, as in equation (16).

$$\vec{R}_{\vec{B}z = \vec{B}z'}$$ (16)

FIG. 6 illustrates the rotation angles. x, y, z is the coordination of coil, or call global coordination; x', y', z' is the coordination of magnetic sensor, or called local coordination. α is the rotation around X axis, called pitch; β is the rotation around Y axis, called yaw; γ is the rotation around Z axis, called roll.

Axis Rotations

First, we look at a rotation around each axis; +X, +Y and +Z. We project three axes onto a plane in 3 different ways, so the axis that we want to rotate is facing toward you. The positive rotation direction becomes counter clockwise (right hand rule).

Figure 20:
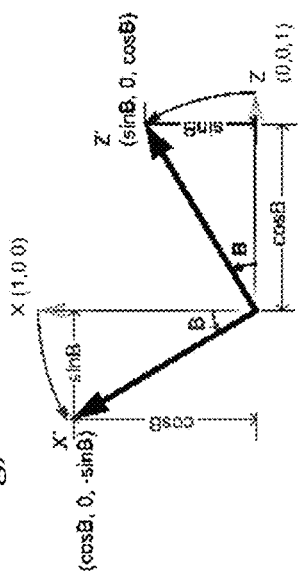
Figure 21:
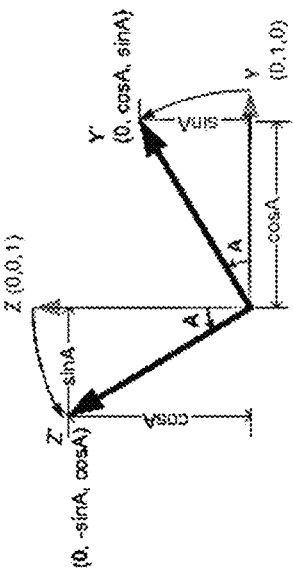
Figure 22:
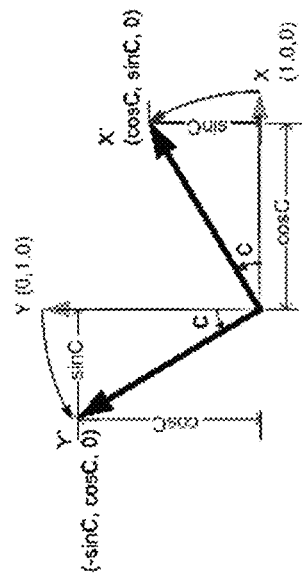

Rotation about Left(X) Axis (Pitch) is depicted in FIG. 20; Rotation about Up(Y) Axis is depicted in FIG. 21; and Rotation about Forward(Z) Axis (Roll) is depicted in FIG. 22.

Initial value of up(Y) and forward(Z) axes are (0, 1, 0) and (0, 0, 1). If left(X) axis rotates A degree, then new up(Y') axis becomes (0, cos A, sin A) and forward(Z') becomes (0, −sin A, cos A). The new axes are inserted as column components of the 3×3 rotation matrix. Then, the rotation matrix becomes;

$$\begin{pmatrix} 1 & 0 & 0 \\ 0 & \cos A & -\sin A \\ 0 & \sin A & \cos A \end{pmatrix}$$

Now, we rotate around up vector, which is facing toward you, with B angle. Left(X) axis is transformed from (1, 0, 0) to X' (cos B, 0, −sin B). And forward(Z) axis is from (0, 0, 1) to Z' (sin B, 0, cos B).

$$\begin{pmatrix} \cos B & 0 & \sin B \\ 0 & 1 & 0 \\ -\sin B & 0 & \cos B \end{pmatrix}$$

If we rotate forward(Z) axis with angle C degree, the original left(X) (1, 0, 0) axis becomes X' (cos C, sin C, 0), and up(Y) (0, 1, 0) axis becomes Y' (−sin C, cos C, 0).

$$\begin{pmatrix} \cos C & -\sin C & 0 \\ \sin C & \cos C & 0 \\ 0 & 0 & 1 \end{pmatrix}$$

Angles To Axes

We can combine these separate axis rotations into one matrix by multiplying above 3 matrices together. Note that multiplication of matrices is not commutative, so a different order of matrix multiplication results in a different outcome. There are 6 different combinations are possible; $R_x R_y R_z$, $R_x R_z R_y$, $R_y R_x R_z$, $R_y R_z R_x$, $R_z R_x R_y$, and $R_z R_y R_x$.

The left column of the combined rotation matrix is the left axis after rotated, the middle column is the up axis, and the right column is the forward axis.

$$R_X R_Y R_Z = \begin{pmatrix} 1 & 0 & 0 \\ 0 & \cos A & -\sin A \\ 0 & \sin A & \cos A \end{pmatrix} \begin{pmatrix} \cos B & 0 & \sin B \\ 0 & 1 & 0 \\ -\sin B & 0 & \cos B \end{pmatrix} \begin{pmatrix} \cos C & -\sin C & 0 \\ \sin C & \cos C & 0 \\ 0 & 0 & 1 \end{pmatrix}$$

$$= \begin{pmatrix} \cos B & 0 & \sin B \\ \sin A \sin B & \cos A & -\sin A \cos B \\ -\cos A \sin B & \sin A & \cos A \cos B \end{pmatrix} \begin{pmatrix} \cos C & -\sin C & 0 \\ \sin C & \cos C & 0 \\ 0 & 0 & 1 \end{pmatrix}$$

$$= \begin{pmatrix} \cos B \cos C & -\cos B \sin C & \sin B \\ \sin A \sin B \cos C + \cos A \sin C & -\sin A \sin B \sin C + \cos A \cos C & -\sin A \cos B \\ -\cos A \sin B \cos C + \sin A \sin C & \cos A \sin B \sin C + \sin A \cos C & \cos A \cos B \end{pmatrix}$$

Wherein the R is the rotation matrix and the Bz is the magnetic field vector in the 3D excitation coil assembly along the z direction (FIG. 6) and Bz' is the magnetic field vector which is measured by the magnetic sensor in the remote object coordination. Further, the rotation matrix R is described as in formulae 17.

$$R(\alpha, \beta, \gamma) = \begin{bmatrix} c_y c_z & c_y s_z & -s_y \\ s_x s_y c_z - c_x s_z & s_x s_y s_z + c_x c_z & s_x c_y \\ c_x s_y c_z - s_x s_z & c_x s_y s_z - s_x c_z & c_x c_y \end{bmatrix} \quad (17)$$

Wherein $\alpha$, $\beta$, and $\gamma$ are the rotation angles.

$s_x = \sin(\alpha)$  $s_y = \sin(\beta)$  $s_z = \sin(\gamma)$ $c_x = \cos(\alpha)$  $c_y = \cos(\beta)$  $c_z = \cos(\gamma)$ Theoretically, by equations (15) and (16), the values of $\alpha$, $\beta$, and $\gamma$ can be calculated. But it may be involving solving multiple nonlinear equations, which is not very effective. Alternatively, the calculation can be simplified, we can mathematically use the linear combination of the magnetic field of X, Y, and Z excitation coils so that the 3D excitation coil assembly magnetic field at the magnetic sensor point is along the z direction. we can also mathematically use the linear combination of the magnetic field of X, Y, and Z excitation coils so that the 3D excitation coil assembly magnetic field at the magnetic sensor point is along the y direction.

XYZ is the denotation of XYZ coils along xyz axis respectively.

$\vec{\vec{R}} \vec{B}_{ext} = \vec{B}'_{int}$ $\vec{\vec{R}}(k_1 \vec{B}_x + k_1 \vec{B}_y + \vec{B}_z) = (k_1 \vec{B}'_x + k_1 \vec{B}'_y + \vec{B}'_z)$ $\vec{\vec{R}}(k_3 \vec{B}_x + k_4 \vec{B}_z + \vec{B}_y) = (k_3 \vec{B}'_x + k_4 \vec{B}'_z + \vec{B}'_y)$ \quad (18)

Wherein $\vec{B}_{ext}$ is the magnetic field in 3D solenoid coordination, which can be along x, Bx, or along y, By or along z, Bz.

$\vec{B}'_{int}$ is the magnetic field in magnetic sensor coordination, which can be for the solenoid along x, Bx', or along y, By' or along z, Bz'.

The linear combination in (18) provides simplification to the calculation in equation (17). Further, by equation groups (19) and (20), a much easier calculation to obtain rotation angle $\alpha$, and $\beta$ are derived, as described in equations (21) and (22).

$$k_1 = \frac{Bz_y By_x - Bz_x By_y}{Bx_x By_y - By_x Bx_y} \quad (19)$$

$$k_2 = \frac{Bz_y Bx_x - Bz_x Bx_y}{By_x Bx_y - By_y Bx_x}$$

$B_z = k_1 Bx_z + k_2 By_z + Bz_z$ $B'_x = Bz'_x + k_1 Bx'_x + k_2 By'_x$ $B'_y = Bz'_y + k_1 Bx'_y + k_2 By'_y$ $B'_z = Bz'_z + k_1 Bx'_z + k_2 By'_z$ $$\vec{B}_{coil} = \begin{bmatrix} 0 \\ 0 \\ B_z \end{bmatrix} \quad (20)$$

$$\vec{B}_{sensor} = \begin{bmatrix} B'_x \\ B'_y \\ B'_z \end{bmatrix}$$

$\vec{\vec{R}} \vec{B}_{coil} = \vec{B}'_{sensor}$

Wherein coil $\vec{B}_{coil}$, $\vec{B}_{sensor}$ are the magnetic field in 3D excitation coil assembly coordination and magnetic sensor coordination respectively. $\vec{B}_{coil}$, $\vec{B}_{sensor}$ sensor are the same as $B_{ext}$ and $B_{int}$ respectively. The angles of the magnetic sensor orientation are $\alpha = \arctan(B'_y / B'_z)$ \quad (21)

$\beta = \arcsin(-B'_x / B_z)$ \quad (22)

Correspondingly, similar procedures can be applied to the 3D solenoid assembly magnetic field along y axis, as described in equations (23). As a result, easier calculation to obtain rotation angle $\gamma$ is derived, as described in equations (25).

$$k_3 = \frac{By_z Bz_x - By_x Bz_z}{Bx_x Bz_z - Bx_z Bz_x} \quad (23)$$

$$k_4 = \frac{By_z Bx_x - By_x Bx_z}{Bz_x Bx_x - Bz_z Bx_x}$$

$B_y = k_3 Bx_y + k_4 Bz_y + Bz_y$ $B''_x = By'_x + k_3 Bx'_x + k_4 Bz'_x$ $B''_y = By'_y + k_3 Bx'_y + k_4 Bz'_y$ $B''_z = By'_z + k_3 Bx'_z + k_4 Bz'_z$ $$\vec{B}_{coil} = \begin{bmatrix} 0 \\ 0 \\ B_z \end{bmatrix} \quad (24)$$

$$\vec{B}'_{sensor} = \begin{bmatrix} B''_x \\ B''_y \\ B''_z \end{bmatrix}$$

$\gamma = \arcsin(B''_x \cos(\beta) / B_y)$ \quad (25)

In summary, by equations (21), (22) and (25), the rotation angles of 3D magnetic sensor in the remote object can be determined. Wherein $B_{coil}$ and $B_{ext}$, $B_{sensor}$ and $B_{int}$ can be used interchangeably.

A system and method to use one three-dimensional magnetic excitation coil assembly to determine a position and orientation of the remote object is disclosed above. In another implementation, under the same operational principle, 3 three-dimensional magnetic coils system can be used to cooperatively determine the position of a remote object in a more accurate manner. An advanced system having 3 three-dimensional magnetic coil assembly system in different locations, surrounding the remote object, can determine the distance between each three-dimensional magnetic coil assembly corporately.

In one embodiment, three sets of 3D excitation coil assemblies are disposed surrounding a target area. In one instance, the three sets of 3D excitation coil assemblies are placed surrounding a patience's body at three different locations. In one example, a first three-dimensional magnetic excitation assembly is positioned at Assume that the at (x1, y1, z1), a second three-dimensional magnetic excitation assembly is placed at (x2, y2, z2), and a third three-dimensional magnetic excitation assembly is placed at (x3, y3, z3). The distance between the first three-dimensional magnetic excitation assembly to the second three-dimensional magnetic excitation assembly is L1, the distance between the second first three-dimensional magnetic excitation assembly to the third three-dimensional magnetic excitation assembly is L2 and the distances between the first three dimensional magnetic excitation assembly to the third three dimensional magnetic excitation assembly is L3.

Then the formula to calculate the location is $$x = \frac{[x_1 - A(B - y_1) - C(D - z_1)] \pm \sqrt{\begin{array}{l}[x_1 - A(B - y_1) - C(D - z_1)]^2 - \\ (1 + A^2 + C^2)[(B - y_1)^2 + (D - z_1)^2 - L_1^2]\end{array}}}{1 + A^2 + C^2} \quad (26)$$

Where $$A = \frac{(x_2 - x_3)(z_1 - z_2) - (x_1 - x_2)(z_2 - z_3)}{(y_1 - y_2)(z_2 - z_3) - (y_2 - y_3)(z_1 - z_2)} \quad (27)$$

$$B = \frac{\frac{1}{2}\left[\begin{array}{l}(L_2^2 - b^2)(z_1 - z_3) - \\ (L_1^2 - a^2)(z_2 - z_3) - (L_3^2 - c^2)(z_1 - z_3)\end{array}\right]}{(y_1 - y_2)(z_2 - z_3) - (y_2 - y_3)(z_1 - z_2)}$$

$$C = \frac{(x_1 - x_2)(y_2 - y_3) - (x_2 - x_3)(y_1 - y_2)}{(y_1 - y_2)(z_2 - z_3) - (y_2 - y_3)(z_1 - z_2)}$$

$$D = \frac{\frac{1}{2}\left[\begin{array}{l}(L_1^2 - a^2)(y_2 - y_3) + \\ (L_3^2 - c^2)(y_1 - y_2) - (L_2^2 - b^2)(y_1 - y_3)\end{array}\right]}{(y_1 - y_2)(z_2 - z_3) - (y_2 - y_3)(z_1 - z_2)}$$

Where
$x_1^2 + y_1^2 + z_1^2 = a^2$
$x_2^2 + y_2^2 + z_2^2 = b^2$
$x_3^2 + y_3^2 + z_3^2 = c^2$
$y = Ax + B$
$z = Cx + D$ Equations (26)-(27) give the (x,y,z) location of the magnetic sensor.

In an alternative embodiment of the present invention, a reference position is used to further identify if the three-dimensional assembly was moved during the location determination period.

In one example, a reference magnetic sensor is taped to a human body, specifically the back lumbar spine when one 3D magnetic excitation assembly is worn around the human's body around the waist as shown in FIG. 3. During the long and repeated location determination process of a remote miniaturized examination device inside the human body, the three-dimensional excitation magnetic coil assembly may dislocation. A method including steps to measure both the distance between the three-dimensional excitation magnetic coil assembly and remote miniaturized examination device, and the distance between the three-dimensional excitation magnetic coil assembly and reference position can remove error due the movement of the three-dimensional excitation magnetic coil assembly. The method comprises the steps of first, determining a distance P from the three-dimensional excitation magnetic coil assembly to the remote object, wherein P is a vector.

Second, determining a distance Q from the three-dimensional excitation magnetic coil assembly to the reference position, wherein Q is a vector.

Then calculating a distance between P(vector)-Q(vector) to remove the error due to the likely movement of the three-dimensional excitation magnetic coil assembly. The measurement of distance P and distance Q happens at the same time.

Remote miniaturized examination devices used for medical implementations may be equipped with one or more of the following: medical diagnostic tools, medical therapy tools, or surgical tools. Medical diagnostic tools are devices that aid in the examination of the bodily conditions of the area in which the remote miniaturized examination device is deployed. These tools can include sensors that take images or measure the temperature, pressure, PH, and the like. In some versions of the invention, medical diagnostic tools may also include devices that collect physical samples from the area and deliver the samples outside of the body for further testing. Medical therapy tools refer to treatment devices meant to treat an existing medical condition. For example, these tools may include drug delivery units, medical light sources for photodynamic therapy, or controlled heat sources for hypothermia therapy. Medical surgical tools include devices that can perform surgical operations in vivo.

The apparatus, systems and methods of the invention provide one or more advantages including but not limited to one or more of, improved remote object orientation and motion control, reduced remote probe power requirements. While the invention has been described with reference to certain illustrative embodiments, those described herein are not intended to be construed in a limiting sense. For example, variations or combinations of features or materials in the embodiments shown and described may be used in particular cases without departure from the invention. Although the presently preferred embodiments are described herein in terms of particular examples, modifications and combinations of the illustrative embodiments as well as other advantages and embodiments of the invention will be apparent to persons skilled in the arts upon reference to the drawings, description, and claims.

The invention claimed is:

1. A method to determining a position and orientation of a remote object in a target area, comprising:
   providing a portable external magnetic field generation assembly,
      bringing the portable external magnetic field generation assembly near to the target area,
      or placing the portable external magnetic field generation assembly near to the target area to cover the remote area, without additional physical mechanical fixtures, and
      generating pulsed magnetic fields respectively in three dimensions;
   introducing a remote object enclosing a 3-dimensional magnetic field sensor into the enclosed or semi-enclosed target area in a digestive channel,
      sensing the pulsed magnetic fields generated externally by the portable external magnetic field generation assembly by the 3-dimensional magnetic field while the remote object is traveling in the enclosed or semi-enclosed target area at a rate;
      measuring the position and orientation of the remote object with an acceptable position accuracy threshold under a confined measurement time limit less than 50 ms;
      executing one or more computer processors configured to performing the steps of
   determining three pure magnetic fields generated by a three-dimensional magnetic excitation assembly;
   calculating the position of the remote object; and
   determining orientation of the remote object,
   wherein the step of calculating the position of the remote object includes determining a current position data P (a, b, c) of the remote object in three coordinates by equation (6)

$$p = A^{1/3}/[((Bx/mx)^2 + (By/my)^2 + Bz^2)/6]^{-1/6} \quad (6)$$

$$a = \pm p \sqrt[x]{((Bx/mx)^2 p^6/A^2 - 1)/3}$$

$$b = \pm p \sqrt{((By/my)^2 p^6/A^2 - 1)/3}$$

$$c = \pm p \sqrt{(Bz^2 p^6/A^2 - 1)/3} \quad (7)$$

wherein p is a distance between
the external magnetic field generation assembly, which located at a position O
and the remote object, which is located at the position P (a, b, c);
Bx is the magnetic field generated in x direction;
By is the magnetic field generated in y direction;
Bz is the magnetic field generated in z direction;
mx is a ratio of magnetic moment from x coil to z coil,
my is a ratio of magnetic moment from y coil to z coil,
wherein magnetic moment of each coil is proportional to
a coil current and an open cross section area of its respective coil and a number of wire turns,
and x coil, z coil and y coil are in the portable external magnetic field generation assembly;
A is defined by $$A = \mu_0/4\pi |\vec{M}|$$

$\mu_0$ is the vacuum magnetic permeability, M is a magnetic moment of an individual excitation coil.

2. The method of claim 1, wherein the step of determining three pure magnetic fields generated by three-dimensional magnetic excitation assembly is accomplished by
measuring an environmental magnetic field data and removing the environmental magnetic field data from measured total magnetic field data of the three-dimensional magnetic assembly, including
measuring an environmental magnetic field vector every time before or/and after a pulsed magnetic field from an excited coil, calibrating the magnetic field vector generated by the external magnetic field generation assembly by removing the environmental magnetic field vector;
a time interval between the environmental magnetic field detection and the pulsed magnetic field from an excited coil shall be less than the half of the period of varying environmental magnetic field.

3. The method of claim 1, wherein the step of determining three pure magnetic fields generated by three-dimensional magnetic excitation assembly is accomplished by
measuring the magnetic field generated by each coil in the magnetic generation assembly in a positive and negative direction, and adding results of the two total magnetic field data lead to cancellation of the environmental magnetic field.

4. The method of claim 1, wherein the step of determining three pure magnetic fields generated by three-dimensional magnetic excitation assembly is accomplished by
a combinatorial sequencing method to measure total magnetic fields three times, and among which at least one electrical current direction for one of the coils is different from the previous sequence.

5. The method of claim 1, wherein the step of calculating the position of the remote object further includes
determining the orientation of remote miniaturized examination $$B_{ext} = \begin{bmatrix} 0 \\ 0 \\ B_z \end{bmatrix} \quad B_{int} = \begin{bmatrix} B'_x \\ B'_y \\ B'_z \end{bmatrix}$$

$$B'_z = -\sin(\beta) B_x$$

$$B'_y = \sin(\alpha)\cos(\beta) B_y$$

$$B'_z = \cos(\alpha)\cos(\beta) B_z$$

$$B_{ext} = \begin{bmatrix} 0 \\ B_y \\ 0 \end{bmatrix} \quad B_{int} = \begin{bmatrix} B'_x \\ B'_y \\ B'_z \end{bmatrix}$$

$$B'_x = \cos(\beta)\sin(\gamma) B_y$$

wherein the position O is a position of the external magnetic field generation assembly, a line from O to P forms angles $\alpha$, $\beta$, $\gamma$, with three axes x, y and z, respectively, in the three coordinates.

6. The method of claim 1, wherein the wherein the acceptable position accuracy target of the 0.5 mm.

7. The method of claim 1, wherein the target area is a digestive channel and remote object travels at a rate of 10 mm/s.

* * * * *